(12) United States Patent
Tomosugi

(10) Patent No.: US 7,297,556 B2
(45) Date of Patent: Nov. 20, 2007

(54) METHOD OF DIAGNOSING NEPHROTIC SYNDROME

(75) Inventor: Naohisa Tomosugi, Kanazawa (JP)

(73) Assignee: Vermillion, Inc., Fremont, CA (US)

( * ) Notice: Subject to any disclaimer, the term of this patent is extended or adjusted under 35 U.S.C. 154(b) by 482 days.

(21) Appl. No.: 10/487,978

(22) PCT Filed: Aug. 29, 2002

(86) PCT No.: PCT/US02/28152

§ 371 (c)(1),
(2), (4) Date: Feb. 27, 2004

(87) PCT Pub. No.: WO03/019193

PCT Pub. Date: Mar. 6, 2003

(65) Prior Publication Data

US 2005/0260678 A1    Nov. 24, 2005

Related U.S. Application Data

(60) Provisional application No. 60/315,774, filed on Aug. 30, 2001.

(51) Int. Cl.
*G01N 33/53* (2006.01)
(52) U.S. Cl. ............... 436/811; 435/7.1; 435/7.92; 436/174
(58) Field of Classification Search .......... 435/6, 435/7.1, 7.92–7.94, 975; 436/501, 518, 174, 436/811
See application file for complete search history.

(56) References Cited

U.S. PATENT DOCUMENTS 5,719,060 A * 2/1998 Hutchens et al. ........... 436/174
6,225,047 B1 * 5/2001 Hutchens et al. ............. 435/5

OTHER PUBLICATIONS

Akhoundi et al., Production and Characterization of monoclonal and polyclonal antibodies to human alpha-2-HS: development of a two-site ELISA test, Journal of Immunological Methods 172 (1994), pp. 189-196.*
Lebreton et al., Serum concentration of Human Alpha 2-HS glycoprotein during the inflammatory process, J. Clin. Invest., vol. 64, Oct. 1979, pp. 1118-1129.*

* cited by examiner

*Primary Examiner*—Long V. Le
*Assistant Examiner*—Gary W. Counts
(74) *Attorney, Agent, or Firm*—Townsend and Townsend and Crew LLP

(57) ABSTRACT

This invention provides organic biomolecule markers (e.g., proteins) useful for differentiating minimal change nephrotic syndrome (MCNS) from focal segmental glomerulosclerosis (FCS), membranous nephrothropy (MN), and membranoproliferative glomerulonephritis (MPGN). This invention also provides organic biomolecule markers useful for evaluating the therapeutic value of agents for treating kidney disease.

4 Claims, 16 Drawing Sheets

METHOD OF DIAGNOSING NEPHROTIC SYNDROME

CROSS-REFERENCES TO RELATED APPLICATIONS

This application is a non-provisional of, and claims the benefit of the priority date of, U.S. application Ser. No. 60/315,774, filed Aug. 30, 2001, the disclosure of which is incorporated herein by reference for all purposes.

BACKGROUND OF THE INVENTION

Idiopathic nephrotic syndromes due to primary glomerular diseases include the minimal change nephrotic syndrome (MCNS), the focal segmental glomerulosclerosis (FGS), the membranous nephropathy (MN), and the membranoproliferative glomerulonephritis (MPGN). Patients with these diseases fall into hypoproteinemia due to the loss of substantial amounts of protein in the urine during the nephrotic stage, and in order to compensate for the loss, protein synthesis is accelerated in the liver.

The four disease types above are finally diagnosed by taking a sample of the kidney (renal biopsy), and testing the sample with a light microscope and an electron microscope, and also testing the sample through the immunofluorescent antibody method. This diagnostic process is a large burden on the patient and requires time and labor for the histological examination.

Therefore, there has been a demand for a diagnosis method for the nephrotic syndromes by using blood serum or urine, which are relatively easily available. The present invention aims at providing a new diagnosis method. Through this method, the patient can be relieved of the biopsy. At the same time, this method enables the distinction between the MCNS and the FGS, in which the clinical feature is similar to MCNS.

BRIEF SUMMARY OF THE INVENTION

The present invention provides, for the first time, sensitive and quick methods and kits that can be used as an aid for diagnosis of MCNS by measuring markers that are differentially present in samples of a MCNS patient and a subject who does not have MCNS (e.g., MN, FGS, IgA nephropathy, or MPGN patients). By monitoring the amount of one or more of these markers, the methods and kits of the invention can determine the subject's pathological status using minute quantities of crude samples. In particular, it has been found that alpha-2-HS glycoprotein beta chain, a protein detected from serum samples as a 5910 Da peak by SELDI mass spectrometry, is a marker for MCNS.

In one aspect, the invention provides methods for aiding the diagnosis of a kidney disease which comprises detecting alpha-2-HS glycoprotein beta chain in a sample; and correlating the detection of the marker or markers with a probable diagnosis of a kidney disease. In one embodiment, the detection is performed by any one of a variety of immunoassays. In a second embodiment, the detection is performed by SELDI MS mass spectrometry.

In another aspect, the invention provides a kit for aiding in the diagnosis of kidney disease, wherein the kit comprises an MS SELDI probe comprising a surface-bound agent capable of binding an antibody; an antibody that specifically binds alpha-2-HS glycoprotein beta chain; and instructions to detect alpha-2-HS glycoprotein beta chain by contacting a sample with the probe having the antibody bound thereto and detecting alpha-2-HS glycoprotein beta chain by mass spectrometry. In one embodiment, the kit comprises a wash solution that removes unbound material from the probe surface. In another embodiment, the kit comprises instructions to correlate the detection of alpha-2-HS glycoprotein beta chain with nephrotic disease.

In still another aspect, the invention provides a kit for aiding in the diagnosis of kidney disease, wherein the kit comprises an ELISA substrate, an antibody that specifically binds alpha-2-HS glycoprotein beta chain; and instructions to detect alpha-2-HS glycoprotein beta chain by contacting a sample with the ELISA substrate having the antibody bound thereto and detecting alpha-2-HS glycoprotein beta chain by ELISA. In one embodiment, the kit comprises a second, labeled antibody that specifically binds alpha-2-HS glycoprotein beta chain. In another embodiment, the kit further comprises instructions to correlate the detection of alpha-2-HS glycoprotein beta chain with nephrotic disease.

In one aspect, the invention provides methods for aiding a MCNS diagnosis, which comprises determining a test amount of a marker in a sample from a subject and determining whether the test amount is a diagnostic amount consistent with a diagnosis of MCNS. A test amount of a single marker or a plurality of markers can be determined in this aspect of the invention.

The markers can have any suitable characteristics, including any apparent molecular weight. For example, these diagnostic markers include polypeptides having an apparent molecular weight of about 2955.3 Da (DA-1), 6116.6 Da (DA-2), 5910.0 Da (DA-3), 2962.5 Da (DB-1), 6130.8 Da (DB-2), or 3161.5 Da (DB-3).

In yet another embodiment, a sample being tested is taken from a subject's blood, serum, urine, semen, seminal fluid, seminal plasma, or tissue extracts. Preferably, the sample is serum or urine.

In yet another embodiment, the methods for diagnosis comprises determining a test amount of a marker in a sample using immunoassay or gas phase ion spectrometry wherein the markers are selected from the group consisting of polypeptides having an apparent molecular weight of about 2955.3 Da (DA-1), 6116.6 Da (DA-2), 5910.0 Da (DA-3), 2962.5 Da (DB-1), 6130.8 Da (DB-2), or 3161.5 Da (DB-3). Preferably, laser desorption mass spectrometry is used.

In another aspect, the invention provides a method for detecting a marker, the method comprising contacting a sample from a subject with a substrate comprising an adsorbent thereon under conditions to allow binding between a marker and the adsorbent, wherein the marker is a polypeptide which is differentially present in samples of a MCNS and a subject who does not have MCNS (e.g., MN, FGS, IgA nephropathy, or MPGN patients), and detecting the marker bound to the adsorbent by gas phase ion spectrometry.

In yet another embodiment, the method further comprises determining the test amount of the marker bound on the probe substrate, and determining whether the test amount is a diagnostic amount consistent with a diagnosis of MCNS.

In yet another aspect, the invention provides a method for detecting a marker in a sample, the method comprising: providing an antibody that specifically binds to the marker, wherein the marker is a polypeptide which is differentially present in samples of a MCNS patient and a subject who does not have MCNS (e.g., a MN, FGS, IgA nephropathy, or MPGN patient), and contacting the sample with the antibody, and detecting the presence of a complex of the antibody bound to the marker. Markers that are differentially present in samples from MCNS patients include polypeptides having an apparent molecular weight of about 2955.3 Da (DA-1), 6116.6 Da (DA-2), 5910.0 Da (DA-3), 2962.5 Da (DB-1), 6130.8 Da (DB-2), or 3161.5 Da (DB-3).

In yet another embodiment, the method further comprises determining the test amount of the marker bound on the probe substrate, and determining whether the test amount is a diagnostic amount consistent with a diagnosis of MCNS.

In yet another aspect, the invention provides a kit for aiding a diagnosis of MCNS, wherein the kit comprises a substrate comprising an adsorbent thereon, wherein the adsorbent is suitable for binding a marker and a washing solution or instructions for making a washing solution, wherein the combination of the adsorbent and the washing solution allows detection of the marker using gas phase ion spectrometry. The kit is capable of allowing determination of a test amount of a marker, wherein the marker is a polypeptide which is differentially present in samples of a MCNS patient and a subject who does not have MCNS (e.g., a MN, FGS, IgA nephropathy, or MPGN patient).

In one embodiment, the substrate in the kit is in the form of a probe which is removably insertable into a gas phase ion spectrometer. In another embodiment, the kit further comprises another substrate which can be used together with the substrate comprising the adsorbent to form a probe which is removably insertable into a gas phase ion spectrometer.

In another embodiment, the kit further comprises instructions for suitable operational parameters.

In yet another embodiment, the substrate comprises a hydrophobic group and an anionic group as an adsorbent. In yet another embodiment, the substrate comprises a hydrophobic group as an adsorbent. In yet another embodiment, the substrate comprises a metal chelating group. In yet another embodiment, the substrate comprises a metal chelating group complexed with a metal ion as an adsorbent. In yet another embodiment, the substrate comprises an antibody that specifically binds to a marker as an adsorbent. In yet another embodiment, the washing solution is an aqueous solution.

In yet another embodiment, the kit comprises an antibody that specifically binds to the marker, and a detection reagent. Optionally, the antibody can be immobilized on a solid support.

In yet another embodiment, the kits can further comprise a standard indicating a diagnostic amount of the marker.

While the absolute identity of many markers is not yet known, such knowledge is not necessary to measure them in a patient sample, because they are sufficiently characterized by, e.g., mass and by affinity characteristics. It is noted that molecular weight and binding properties are characteristic properties of these markers and not limitations on means of detection or isolation. Furthermore, using the methods described herein or other methods known in the art, the absolute identity of the markers can be determined.

The present invention provides a method for evaluating the progress of kidney disease and the therapeutic value of agents used to treat kidney disease by comparing the results of measurement of markers conducted with samples taken from the same patient before and after MCNS treatment. In the measurement graph, there is a high peak and low peak after treatment. By using these peaks as markers, it is possible to evaluate the progress of the disease and the therapeutic value of agents used to treat the disease.

The markers can have any suitable characteristics, including any apparent molecular weight. For example, these therapeutic markers include polypeptides having an apparent molecular weight of about 2952.3 Da (TA-1), 5910.0 Da (TA-2), 5922.6 Da (TB-1), 10224.4 Da (TB-2), 10793.3 Da (TB-3), 13672.1 Da (TC-1), 13980.1 Da (TC-2), 13895.6 Da (TC-3), 13788.5 Da (TC-4), or 13965.4 Da (TC-5).

In another embodiment, the sample being tested is taken from a subject's blood, serum, urine, semen, seminal fluid, seminal plasma, or tissue extracts. Preferably, the sample is serum or urine.

In yet another embodiment, the methods for evaluating the progress of kidney disease and the therapeutic value of agents used to treat kidney disease comprises determining a test amount of a marker in a sample using immunoassay or gas phase ion spectrometry wherein the markers are selected from the group consisting of polypeptides having an apparent molecular weight of about 2952.3 Da (TA-1), 5910.0 Da (TA-2), 5922.6 Da (TB-1), 10224.4 Da (TB-2), 10793.3 Da (TB-3), 13672.1 Da (TC-1), 13980.1 Da (TC-2), 13895.6 Da (TC-3), 13788.5 Da (TC-4), or 13965.4 Da (TC-5). Preferably, laser desorption mass spectrometry is used.

In yet another aspect, the invention provides a kit for aiding in evaluating the progress of the disease and the therapeutic value of agents used to treat kidney disease, wherein the kit comprises a substrate comprising an adsorbent thereon, wherein the adsorbent is suitable for binding a marker and a washing solution or instructions for making a washing solution, wherein the combination of the adsorbent and the washing solution allows detection of the marker using gas phase ion spectrometry. The kit is capable of allowing determination of a test amount of a marker, wherein the marker is a polypeptide which is differentially present in samples of a kidney disease patient before and after treatment.

In one embodiment, the substrate in the kit is in the form of a probe which is removably insertable into a gas phase ion spectrometer. In another embodiment, the kit further comprises another substrate which can be used together with the substrate comprising the adsorbent to form a probe which is removably insertable into a gas phase ion spectrometer.

In another embodiment, the kit further comprises instructions for suitable operational parameters.

In yet another embodiment, the substrate comprises a hydrophobic group and an anionic group as an adsorbent. In yet another embodiment, the substrate comprises a hydrophobic group as an adsorbent. In yet another embodiment, the substrate comprises a metal chelating group. In yet another embodiment, the substrate comprises a metal chelating group complexed with a metal ion as an adsorbent. In yet another embodiment, the substrate comprises an antibody that specifically binds to a marker as an adsorbent. In yet another embodiment, the washing solution is an aqueous solution.

In yet another embodiment, the kit comprises an antibody that specifically binds to the marker, and a detection reagent. Optionally, the antibody can be immobilized on a solid support.

In yet another embodiment, the kits can further comprise a standard indicating a treatment amount of the marker.

While the absolute identity of many markers is not yet known, such knowledge is not necessary to measure them in a patient sample, because they are sufficiently characterized by, e.g., mass and by affinity characteristics. It is noted that molecular weight and binding properties are characteristic properties of these markers and not limitations on means of detection or isolation. Furthermore, using the methods described herein or other methods known in the art, the absolute identity of the markers can be determined.

These and other aspects of the present invention will become apparent upon reference to the following detailed description and attached drawings.

BRIEF DESCRIPTION OF THE DRAWINGS

In FIG. 1A, the MCNS graph has a peak at 2955.3 Da (DA-1).

In FIG. 2A, the MCNS graph has a peak at 6116.6 Da (DA-2).

In FIG. 3A, the MCNS graph has a peak at 5910 Da (DA-3).

In FIG. 4A, the MCNS graph has peaks at 2962.5 Da (DB-1) and 3161.5 Da (DB-3).

In FIG. 5A, the MCNS graph has a peak at 6130.8 Da (DB-2).

In FIG. 6, the peak at 2952 Da (TA-1) of the serum graph has different height before and after treatment.

In FIG. 7, the peak at 5910 Da (TA-2) has different height before and after treatment.

In FIG. 8, the peak at 5920 Da (TB-1) of the serum graph has different height before and after treatment.

In FIG. 9, the peaks at 10224.4 Da (TB-2) and 10793.3 Da (TB-3) of the serum graph have different height before and after treatment. The peak at 10793.3 Da (TB-3) has higher value after treatment.

In FIG. 10, the peaks at 13672.1 Da (TC-1) and 139801.1 Da (TC-2) of the serum graph have different height before and after treatment. These peaks have higher values after treatment. In FIG. 10, the peak at 13895.6 Da (TC-3) of the urine graph has different height before and after treatment. In FIG. 10, the peaks at 13788.5 Da (TC-4) and 13965.4 Da (TC-5) of the PBNC graph have different height before and after treatment. These peaks have higher values after treatment.

DEFINITIONS

Figure 1A:
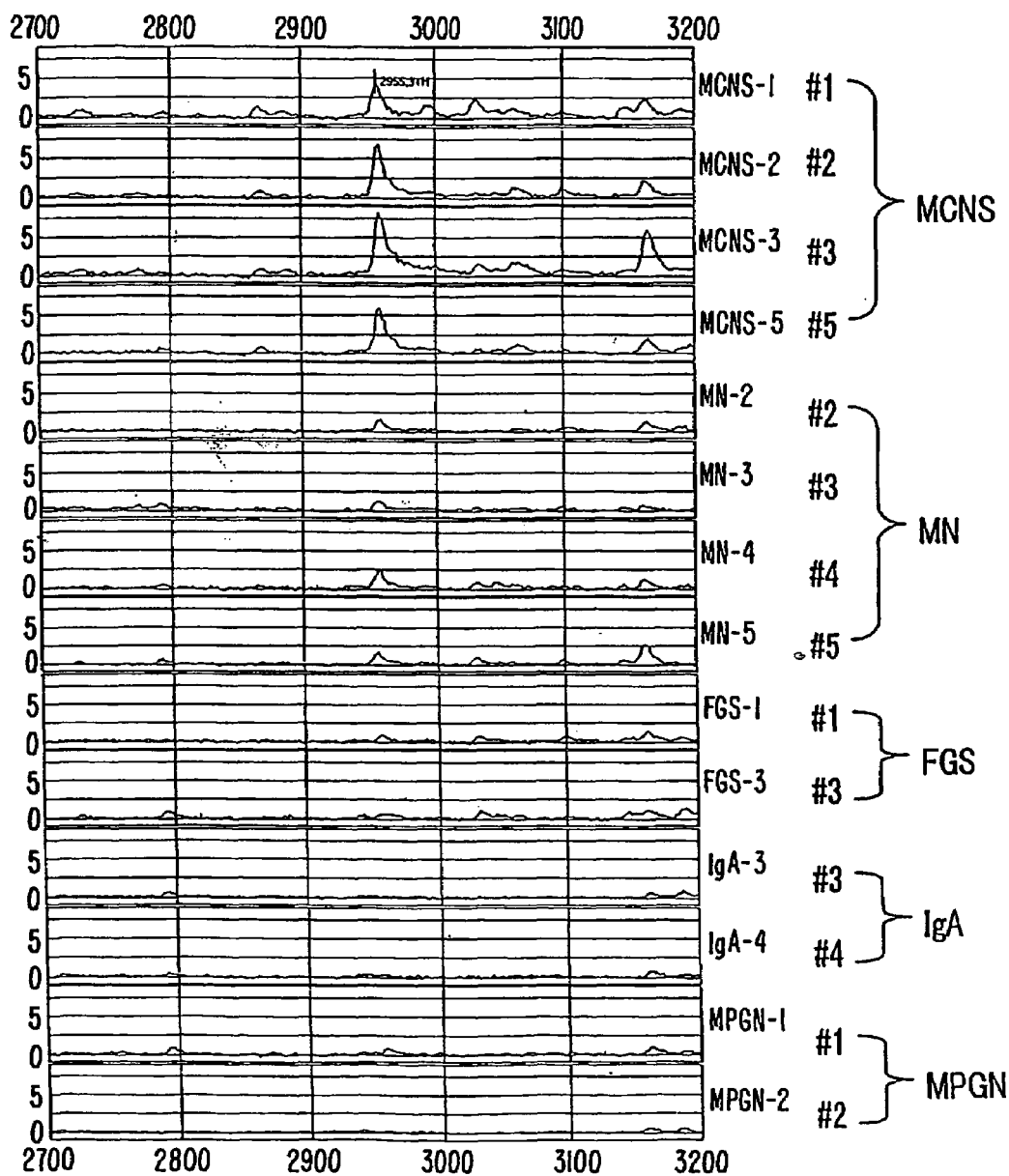
FIG. 1A is a graph comparing four examples of MCNS with four examples of membranous nephropathy (MN), two examples of focal segmental glomerulosclerosis (FGS), two examples of IgA nephropathy, and two examples of membranoproliferative glomerulonephritis (MPGN).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); Cambridge Dictionary of Science and Technology (Walker ed., 1988); The Glossary of Genetics, 5th Ed., R. Rieger el al. (eds.), Springer Verlag (1991); and Hale & Marham, The Harper Collins Dictionary of Biology (1991). As used herein, the following terms have the meanings ascribed to them unless specified otherwise.

"Marker" in the context of the present invention refers to an organic biomolecule, e.g., a polypeptide, which is differentially present in a sample taken from patients having MCNS as compared to a comparable sample taken from subjects who do not have MCNS (e.g., MN, FGS, IgA nephropathy, or MPGN patients or healthy subjects). For examples, a marker can be a polypeptide (having a particular apparent molecular weight) which is present at an elevated level in samples of MCNS patients compared to samples of MN, FGS, IgA nephropathy, or MPGN patients. In another examples, a marker can be a polypeptide (having a particular apparent molecular weight) which is present at an elevated level in samples of MN, FGS, IgA nephropathy, or MPGN patients compared to samples of MCNS patients.

A protein marker is resolved with confidence of about 0.5% variation by gas phase ion spectrometry. Thus, the term "about" in the context of a molecular weight of a marker as measured by mass spectrometry refers to 0.5% variation of the marker molecular weight. For example, the marker with an apparent molecular weight of "about 2776 Da" as measured by mass spectrometry has the apparent molecular weight range of 2776±14 Da; the marker with an apparent molecular weight of "about 4423 Da" as measured by mass spectrometry has the apparent molecular weight range of 4423±22 Da; and so on.

The phrase "differentially present" refers to differences in the quantity and/or frequency of a polypeptide (of a particular apparent molecular weight) present in a sample taken from patients having MCNS as compared to a comparable sample taken from patients who do not have MCNS (e.g., have MN, FGS, IgA nephropathy, or MPGN). For example, a marker can be a polypeptide which is present at an elevated level or at a decreased level in samples of MCNS patients compared to samples of subjects who do not have MCNS. Alternatively, a marker call be a polypeptide which is detected at a higher frequency or at a lower frequency in samples of MCNS patients compared to samples of subjects who do not have MCNS. A marker can be differentially present in terms of quantity, frequency or both.

A polypeptide is differentially present between the two sets of samples if the frequency of detecting the polypeptide in the MCNS patients' samples is statistically significantly higher or lower than in the control samples. In another example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

Alternatively or additionally, a polypeptide is differentially present between the two samples if the amount of the polypeptide in one sample is statistically significantly different from the amount of the polypeptide in the other sample. For example, a polypeptide is differentially present between the two samples if it is present in one sample at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., pg/ml) or a relative amount (e.g., relative intensity of signals).

A "diagnostic amount" of a marker in the context of the present invention refers to an amount of a marker in a subject's sample that is consistent with a diagnosis of MCNS. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a MCNS patient, a MN, FGS, IgA nephropathy, or MPGN patient or a person without MCNS or MN, FGS, IgA nephropathy, or MPGN. A control amount can be either in absolute amount (e.g., µg/ml) or a relative amount (e.g., relative intensity of signals).

"Solid support" refers to any insoluble surface including beads or plastic strips.

"MS probe" refers to a device that, when positionally engaged in an interrogatable relationship to an ionization source, e.g., a laser desorption/ionization source, and in concurrent communication at atmospheric or subatmospheric pressure with the detector of the preferred Laser Desorption/Ionization Time-Of-Flight spectrometer, can be used to introduce ions derived from an analyte into the spectrometer. Preferred laser sources include nitrogen lasers, Nd-Yag lasers and other pulsed laser sources. As used herein, the "MS probe" is typically reversibly engageable (e.g., removably insertable) with a probe interface that positions the MS probe in an interrogatable relationship with the ionization source and in communication with the detector.

"SELDI MS probe" refers to an MS probe comprising an adsorbent surface.

"Adsorbent" or "adsorbent surface" refers to any material capable of binding an analyte (e.g., a target polypeptide). For example, a surface feature on a SELDI MS probe solid support or substratum can comprise an adsorbent attached thereto characterized by various adsorbent species that can each be categorized as either chromatographic or biospecific, depending upon the nature of the binding interaction. Chromatographic adsorbents include ion exchange materials, metal chelators, hydrophobic interaction adsorbents, hydrophilic interaction adsorbents, or the like. "Biospecific adsorbents," include affinity adsorbents such as polypeptides, enzymes, receptors, antibodies (e.g., poly- or monoclonal antibodies, etc.), or the like, and typically have higher specificity for a target analyte than a "chromatographic adsorbent". Examples of adsorbents for use in SELDI are also described in the U.S. Pat. No. 6,225,047 (Hutchens and Yip, "Use of retentate chromatography to generate difference maps," May 1, 2001)

The term "affinity molecule" refers to a molecular substance capable of binding other molecules either specifically or nonspecifically.

"Wash solution" refers to solutions that are applied to a sample bound to a solid support to selectively remove sample fractions. Wash solutions are typically buffered to maintain constant pH, and/or metal ion concentration, etc., but do not have to be.

"Gas phase ion spectrometer" refers to an apparatus that detects gas phase ions. In the context of this invention, gas phase ion spectrometers include an ionization source used to generate the gas phase ions. Gas phase ion spectrometers include, for example, mass spectrometers, ion mobility spectrometers, and total ion current measuring devices.

"Gas phase ion spectrometry" refers to a method that includes employing an ionization source to generate gas phase ions from an analyte presented on a sample presenting surface of a probe and detecting the gas phase ions with a gas phase ion spectrometer.

"Ionization source" refers to a device that directs ionizing energy to a sample presenting surface of a probe to desorb and ionize analytes from the probe surface into the gas phase. The preferred ionization source is a laser (used in laser desorption/ionization), in particular, nitrogen lasers, Nd-Yag lasers and other pulsed laser sources. Other ionization sources include fast atoms (used in fast atom bombardment), plasma energy (used in plasma desorption) and primary ions generating secondary ions (used in secondary ion mass spectrometry).

"Mass spectrometer" refers to a gas phase ion spectrometer that measures a parameter which can be translated into mass-to-charge ratios of gas phase ions. Mass spectrometers generally include an inlet system, an ionization source, an ion optic assembly, a mass analyzer, and a detector. Examples of mass spectrometers are time-of-flight, magnetic sector, quadrapole filter, ion trap, ion cyclotron resonance, electrostatic sector analyzer and hybrids of these.

"Laser desorption mass spectrometer" refers to a mass spectrometer which uses laser as a means to desorb, volatilize, and ionize an analyte.

"Fluence" refers to the energy delivered per unit area of interrogated image.

"Desorption/ionization" refers to generating ions by desorbing them from a solid or liquid sample with a high-energy particle beam (e.g., a laser). Desorption ionization encompasses various techniques including, e.g., surface enhanced laser desorption, matrix-assisted laser desorption, fast atom bombardment, plasma desorption, or the like.

"Surface-enhanced laser desorption/ionization" or "SELDI" is a method of gas phase ion spectrometry in which the surface of substrate which presents the analyte to the energy source plays an active role in the desorption and ionization process. The SELDI technology is described in, e.g., U.S. Pat. No. 5,719,060 (Hutchens and Yip) and U.S. Pat. No. 6,225,047 (Hutchens and Yip).

"Adsorb" refers to the detectable binding between an absorbent and a marker either before or after washing with an eluant (selectivity threshold modifier) or a washing solution.

"Resolve," "resolution," or "resolution of marker" refers to the detection of at least one marker in a sample. Resolution includes the detection of a plurality of markers in a sample by separation and subsequent differential detection. Resolution does not require the complete separation of a marker from all other markers in a mixture. Rather, any separation that allows the distinction between at least two markers suffices.

"Detect" refers to identifying the presence, absence or amount of the object to be detected.

"Retention" refers to an adsorption of a marker or by an adsorbent after washing with an eluant or a washing solution.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known thee letter symbols or by the one-letter symbols recommended by the IUPAC-TUB Biochemical Nomenclature Commission.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavidin, digoxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavidin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g. P. D. Fahrlander and A. Klausner, Bio/Technology 6:1165 (1988)). Quantization of the signal is achieved by, e.g., scintillation counting, densitometry, or now cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. The includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

Methods for preparing antibodies are well-known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

DETAILED DESCRIPTION OF THE INVENTION

The present invention is based upon the discovery of diagnostic markers that are differentially present in the samples of MCNS patients and subjects who do not have MCNS (e.g., have MN, FGS, IgA nephropathy, or MPGN), and the application of this discovery in the methods and kits for aiding a MCNS diagnosis. The present invention is also based upon the discovery that the amount of therapeutic markers measured in samples taken from a patient before and after treatment may change due to the treatment. By monitoring the amount of one or more diagnostic or therapeutic markers in a sample taken from a subject, the methods and kits of the invention can determine the subject's pathological status. The methods and kits of the invention can also be used in addition to conventional MCNS testing methods to confirm the presence or absence of MCNS. The methods of the invention can be performed in a short amount of time using minute quantities of easily obtained biological samples such as blood, serum, urine, semen, seminal fluid, or tissue extracts.

The markers of the present invention may have any suitable characteristics, including any apparent molecular weights. For example, some suitable markers are present at an elevated level in samples of MCNS patients compared to samples of MN, FGS, IgA nephropathy, or MPGN patients. These markers may be found in a number of biological samples, and markers found in serum are preferably monitored in the methods and kits of the invention.

Each of the markers can have particular binding characteristics which allow these markers to be enriched and measured in a sample taken from a subject under selectivity conditions that favor binding of these markers.

I. Methods for Detecting Markers Using Gas Phase Ion Spectrometry

In one aspect, the invention provides methods for detecting markers which are differentially present in samples of a MCNS patient and a person who does not have MCNS (e.g., MN, FGS, IgA nephropathy, or MPGN patient). Any one or combination of markers described are within the scope of this aspect of this invention and can be detected. The methods for detecting these markers have many applications. For example, one marker or combination of markers can be measured to differentiate between MCNS and MN, FGS, IgA nephropathy, or MPGN, and thus are useful as an aid in the diagnosis of MCNS in a patient. In another example, the present methods for detecting these markers can be applied to in vitro MCNS cells or in vivo animal models for MCNS to assay for and identify compounds that modulate expression of these markers.

In another aspect, the invention provides for methods for evaluating the progress of the disease and the therapeutic value of agents used to treat kidney disease by measuring the amount of therapeutic markers in samples taken from a patient before and after treatment. The amount of the markers may change due to the treatment. Therapeutic markers are differentially present in a sample obtained from a patient before and after treatment.

A. Gas Phase Ion Spectrometry Detection

In one embodiment of the detection method, a gas phase ion spectrometer can be used. This method comprises: (a) contacting a sample with a substrate comprising an adsorbent thereon under conditions to allow binding between a marker and the adsorbent; and (b) detecting the marker bound to the adsorbent by gas phase ion spectrometry.

The detection of these markers can be enhanced using certain selectivity conditions (e.g., types of adsorbents used or washing solutions). In a preferred embodiment, the same or substantially the same selectivity conditions that were used to discover the markers can be used in the methods for detecting a marker in a sample. For example, a substrate comprising an adsorbent having a hydrophobic group and an anionic group (e.g., polystyrene latex beads functionalized with a sulfonate group) can be used. In another example, a substrate comprising an adsorbent having a hydrophobic group (e.g., an aliphatic C16 hydrocarbon group) can be used. In yet another example, a substrate comprising an adsorbent having a metal ion bound to a metal chelating group (e.g., nickel metal ions chelated by nitrilotriacetic acid groups) as adsorbents can be used. In some embodiments, an adsorbent can be antibodies that specifically bind to the markers. Preferably, a sample is serum taken from a subject.

In one embodiment, a substrate comprising an adsorbent can be in the form of a probe, which is removably insertable into a gas phase ion spectrometer. For example, a substrate can be in the form of a strip with adsorbents on its surface. In another embodiment, a substrate comprising an adsorbent can be positioned onto another substrate to form a probe, which is removably insertable into a gas phase ion spectrometer. For example, a substrate comprising an adsorbent can be a solid phase, such as a polymeric or glass bead with a functional group for binding a marker, which can be subsequently positioned on a second substrate to form a probe. For example, the second substrate can be in the form of a strip, or a plate having a series of wells at a predetermined addressable locations. One advantage of this embodiment is that the marker can be adsorbed to the first substrate in one physical context, and transferred to the second substrate, which can then be submitted for analysis by gas phase ion spectrometry. The probe can be in any shape as long as it is removably insertable into a gas phase ion spectrometer.

The probe can also be adapted for use with inlet systems and detectors of a gas phase ion spectrometer. For example, the probe can be adapted for mounting in a horizontally and/or vertically translatable carriage that horizontally and/or vertically moves the probe to a successive position without requiring repositioning of the probe by hand.

The probe substrate is preferably made of a material that is capable of supporting adsorbents. For example, the probe substrate material can include, but is not limited to, insulating materials (e.g., glass, ceramic), semi-insulating materials (e.g., silicon wafers), or electrically conducting materials (e.g., metals, such as nickel, brass, steel, aluminum, gold, or electrically conductive polymers), organic polymers, biopolymers, or any combinations thereof.

The probe substrate surface can be conditioned to bind markers. For example, in one embodiment, the surface of the probe substrate can be conditioned (e.g., chemically or mechanically such as roughening) to place adsorbents on the surface. The adsorbent comprises functional groups for binding with a marker. In some embodiments, the substrate material itself can also contribute to adsorbent properties and may be considered part of an "adsorbent."

Any number of different adsorbents can be used as long as they have binding characteristics suitable for binding the markers of the present invention. The adsorbents can comprise a hydrophobic group, a hydrophilic group, a cationic group, an anionic group, a metal ion chelating group, or antibodies which specifically bind to antigens, or a combination thereof (sometimes referred to as "a mixed mode" adsorbent). Exemplary adsorbents comprising a hydrophobic group include matrices having aliphatic hydrocarbons, e.g., C1-C18 a aliphatic hydrocarbons and matrices having aromatic hydrocarbon functional group such as phenyl groups. Exemplary adsorbents comprising a hydrophilic group include silicon oxide (i.e., glass), or hydrophilic polymers such as polyethylene glycol, dextran, agarose, or cellulose. Exemplary adsorbents comprising a cationic group include matrices of secondary, tertiary or quaternary amines. Exemplary adsorbents comprising an anionic group include matrices of sulfate anions ($SO_3^-$) and matrices of carboxylate anions (i.e., $COO^-$) or phosphate anions ($OPO_3^-$). Exemplary adsorbents comprising metal chelating groups include organic molecules that have one or more electron donor groups which form coordinate covalent bonds with metal ions, such as copper, nickel, cobalt, zinc, iron, and other metal ions such as aluminum and calcium. Exemplary adsorbents comprising an antibody include antibodies that are specific for any one of the markers provided herein. In preferred embodiments, adsorbents are substantially similar to or the same as the adsorbents which were used to enrich and identify the markers.

Adsorbents can be placed on the probe substrate in continuous or discontinuous patterns. If continuous, one or more adsorbents can be placed on the substrate surface. If multiple types of adsorbents are used, the substrate surface can be coated such that one or more binding characteristics vary in one or two-dimensional gradient. If discontinuous, plural adsorbents can be placed in predetermined addressable locations on the substrate surface. The addressable locations can be arranged in any pattern, but are preferably in regular pattern, such as lines, orthogonal arrays, or regular curves (e.g., circles). Each addressable location may comprise the same or different adsorbent.

The probes can be produced using any suitable methods depending on the selection of substrate materials and/or adsorbents. For example, the surface of a metal substrate can be coated with a material that allows derivitization of the metal surface. More specifically, a metal surface can be coated with silicon oxide, titanium oxide or gold. Then surface can be derivatized with a bifunctional linker, one end of which can covalently bind with a functional group on the surface and the other end of which can be further derivatized with groups that function as an adsorbent. In another example, a porous silicon surface generated from crystalline silicon can be chemically modified to include adsorbents for binding markers. In yet another example, adsorbents with a hydrogel backbone can be formed directly on the substrate surface by in situ polymerizing a monomer solution which comprises, e.g., substituted acrylamide monomers, substituted acrylate monomers, or derivatives thereof comprising a functional group of choice as an adsorbent.

Probes suitable for use in the invention are also described in, e.g., WO98/59361, U.S. Ser. No. 60/131,652, filed Apr. 29, 1999, and Wei et al., Nature 399:243-30 246 (1999).

The probe substrate comprising an adsorbent contacts a sample. The sample is preferably a biological fluid sample. Examples of biological fluid samples include blood, serum, urine, semen, seminal fluid or tissue extracts. In a preferred embodiment, the biological fluid comprises serum.

The sample can be solubilized in or admixed with an eluant. The probe substrate comprising an adsorbent then contacts the solution using any techniques including bathing, soaking, dipping, spraying, washing over, or pipetting, etc. Generally, a volume of sample containing from a few attomoles to 100 picomoles of marker in about 1 µl to 500 µl is sufficient for binding to the adsorbent.

The sample can contact the probe substrate comprising an adsorbent for a period of time sufficient to allow the marker to bind to the adsorbent. Typically, the sample and the substrate comprising the adsorbent are contacted for a period of between about 30 seconds and about 12 hours, and preferably, between about 30 seconds and about 15 minutes.

The temperature at which the sample contacts the probe substrate comprising an adsorbent can be a function of the particular sample and the selected probe. Typically, the sample is contacted to the probe substrate under ambient temperature and pressure conditions. For some samples, however, modified temperature (typically 4° C. through 37° C.), and pressure conditions can be desirable, which conditions are determinable by those skilled in the art.

After the probe substrate comprising an adsorbent contacts the sample or sample solution, it is preferred that unbound materials on the probe substrate surface are washed out so that only the bound materials remain on the substrate surface. Washing a probe substrate surface can be accomplished by, e.g., bathing, soaking, dipping, rinsing, spraying, or washing the substrate surface with an eluant or a washing solution. A microfluidics process is preferably used when a washing solution such as an eluant is introduced to small spots of adsorbents on the probe. Typically, the washing solution can be at a temperature of between 0° C. and 100° C., preferably between 4° C. and 37° C.

Any suitable washing solutions or eluants can be used to wash the probe substrate surface. For example, organic solutions or aqueous solutions can be used. Preferably, an aqueous solution is used. Exemplary aqueous solutions include a HEPES buffer, a Tris buffer, a phosphate buffered saline, etc. The selection of a particular washing solution or an eluant is dependent on other experimental conditions (e.g., types of adsorbents used or markers to be detected), and can be determined by those of skill in the art. For example, if a probe comprising a hydrophobic group and a sulfonate group as adsorbents is used, then an aqueous solution, such as a HEPES buffer, may be preferred. In another example, if a probe comprising a metal binding group as an adsorbent is used. then an aqueous solution, such as a phosphate buffered saline, may be preferred. In yet another example, if a probe comprising a hydrophobic group is used, then water may be preferred as a washing solution.

Optionally, an energy absorbing molecule (e.g., in solution) can be applied to markers or other substances bound on the probe substrate surface. Spraying, pipetting, or dipping can be used. This can be done after unbound materials are washed off of the probe substrate surface. An energy absorbing molecule refers to a molecule that absorbs energy from an energy source in a gas phase ion spectrometer, thereby assisting desorption of markers or other substances from a probe surface. Exemplary energy absorbing molecules include cinnamic acid derivatives, sinapinic acid and dihydroxybenzoic acid.

After the marker is bound to the probe, it is detected using gas phase ion spectrometry. Markers or other substances bound to the adsorbents on the probes can be analyzed using a gas phase ion spectrometer. This includes, e.g., mass spectrometers, ion mobility spectrometers, or total ion current measuring devices. The quantity and characteristics of the marker can be determined using gas phase ion spectrometry. Other substances in addition to the marker of interest can also be detected by gas phase ion spectrometry.

In one embodiment, a mass spectrometer can be used to detect markers on the probe. In a typical mass spectrometer, a probe with a marker is introduced into an inlet system of the mass spectrometer. The marker is then ionized by an ionization source such as a laser, fast atom bombardment, or plasma. The generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of a marker or other substances will typically involve detection of signal intensity. This, in turn, can reflect the quantity and character of a marker bound to the probe.

In a preferred embodiment, a laser desorption time-of-flight mass spectrometer is used with the probe of the present invention. In laser desorption mass spectrometry, a probe with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ionization and impact can be used to identify the presence or absence of molecules of specific mass. As any person skilled in the art understands, any of these components of the laser desorption time-of-flight mass spectrometer can be combined with other components described herein in the assembly of mass spectrometer that employs various means of desorption, acceleration, detection, measurement of time, etc.

In another embodiment, an ion mobility spectrometer can be used to detect and characterize a marker. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in the sample. One advantage of ion mobility spectrometry is that it can operate at atmospheric pressure.

In yet another embodiment, a total ion current measuring device can be used to detect and characterize markers. This device can be used when the probe has a surface chemistry that allows only a single type of marker to be bound. When a single type of marker is bound on the probe, the total current generated from the ionized marker reflects the nature of the marker. The total ion current produced by the marker can then be compared to stored total ion current of known compounds. Characteristics of the marker can then be determined.

Data generated by desorption and detection of markers can be analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. Using this information, the program can then identify the set of features on the probe defining certain selectivity characteristics (e.g., types of adsorbent and eluants used). The computer also contains code that receives as input, data on the strength of the signal at various molecular masses received from a particular addressable location on the probe. This data can indicate the number of markers detected, optionally including the strength of the signal and the determined molecular mass for each marker detected.

Data analysis can include the steps of determining signal strength (e.g., height of peaks) of a marker detected and removing "outerliers" (data deviating from a predetermined statistical distribution). For example, the observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other substances can be displayed in the form of relative intensities in the scale desired (e.g., 100). Alternatively, a standard may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoresis gels. In yet another format, referred to as "3-D overlays," several spectra can be overlayed to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually.

Using any of the above display formats, it can be readily determined from the signal display whether a diagnostic marker having a particular molecular weight (e.g., about 2955.3 Da (DA-1), 6116.6 Da (DA-2), 5910.0 Da (DA-3), 2962.5 Da (DB-1), 6130.8 Da (DB-2), or 3161.5 Da (DB-3)) is detected from a sample. Alternatively, it can be readily determined from the signal display whether a therapeutic marker having an apparent molecular weight of about 2952.3 Da (TA-1), 5910.0 Da (TA-2), 5922.6 Da (TB-1), 10224.4 Da (TB-2), 10793.3 Da (TB-3), 13672.1 Da (CA-1), 13980.1 Da (CA-2), 13895.6 Da (CA-3), 13788.5 Da (CA-4), or 13965.4 Da (CA-5) is detected from a sample. Moreover, from the strength of signals, the amount of diagnostic or therapeutic markers bound on the probe surface can be determined.

B. Immunoassay Detection

In another embodiment of the detection method, an immunoassay can be used to qualitatively or quantitatively detect and analyze diagnostic or therapeutic markers in a sample. This method comprises: (a) providing an antibody that specifically binds to a marker, wherein the marker is a polypeptide which is differentially present in samples of a MCNS patient and a subject who does not have MCNS (e.g., MN, FGS, IgA nephropathy, or MPGN patients) or is differentially present in a sample obtained from a patient before and after treatment; (b) contacting a sample with the antibody, and (c) detecting the presence of a complex of the antibody bound to the marker in the sample.

To prepare an antibody that specifically binds to a marker, purified markers or their nucleic acid sequences can be used. Nucleic acid and amino acid sequences for other markers can be obtained by further characterization of these markers. For example, each marker can be peptide mapped with a number of enzymes (e.g., trypsin, V8 protease, etc.). The molecular weights of digestion fragments from each marker can be used to search the databases, such as SwissProt database, for sequences that will match the molecular weights of digestion fragments generated by various enzymes. Using this method, the nucleic acid and amino acid sequences of other markers can be identified if these markers are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 (Chait et al.) and U.S. Pat. No. 5,792,664 (Chait et al.). The ladder is then analyzed by mass spectrometry. The difference in the masses of the ladder fragments identify the amino acid removed from the end of the molecule.

If the markers are not known proteins in the databases, nucleic acid and amino acid sequences can be determined with knowledge of even a portion of the amino acid sequence of the marker. For example, degenerate probes can be made based on the N-terminal amino acid sequence of the marker. These probes can then be used to screen a genomic or cDNA library created from a sample from which a marker was initially detected. The positive clones can be identified, amplified, and their recombinant DNA sequences can be subcloned using techniques which are well known. See, e.g., Current Protocols for Molecular Biology (Ausbel et al., Green Publishing Assoc. and Wiley-Interscience 1989) and Molecular Cloning: A Laboratory Manual, 2nd Ed. (Sambrook el al., Cold Spring Harbor Laboratory, New York 1989).

Using the purified markers or their nucleic acid sequences, antibodies that specifically bind to a marker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)).

After the antibody is provided, a marker can be detected and/or quantified using any of a number of well recognized immunological binding assays (see, e.g., U.S. Pat. Nos. 4,366,2411 4,376,110; 4,517,288; and 4,837,168). Useful assays include, for example, an enzyme immune assay (EIA) such as enzyme-linked immunosorbent assay (ELISA), a radioimmune assay (NA), a Western blot assay, or a slot blot assay. For a review of the general immunoassays, see also, Methods in Cell Biology: Antibodies in Cell Biology, volume 37 (Asai, ed. 1993); Basic and Clinical Immunology (Stites & Terr, eds., 7th ed. 1991); Harlow & Lane, Antibodies, A Laboratory Manual (1988).

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include blood, serum, urine, semen, seminal fluid or tissue extracts. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine the presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid MCNS diagnosis or prognosis. For example, these diagnostic markers include polypeptides having an apparent molecular weight of about 2955.3 Da (DA-1), 6116.6 Da (DA-2), 5910.0 Da (DA-3), 2962.5 Da (DB-1), 6130.8 Da (DB-2), or 3161.5 Da (DB-3). In another example, the methods for detection of the markers can be used to monitor responses in a subject to MCNS therapeutic treatment For example, these therapeutic markers include polypeptides having an apparent molecular weight of about 2952.3 Da (TA-1), 5910.0 Da (TA-2), 5922.6 Da (TB-1), 10224.4 Da (TB-2), 10793.3 Da (TB-3), 13672.1 Da (CA-1), 13980.1 Da (CA-2), 13895.6 Da (CA-3), 13788.5 Da (CA-4), or 13965.4 Da (CA-5). In another example, the methods for detecting markers can be used to assay for and to identify compounds that modulate expression of these markers in vivo or in vitro.

II. Methods for Diagnosing MCNS Using Test Amount of Markers

In another aspect, the invention provides methods for aiding a MCNS diagnosis using a marker which is differentially present in samples of a MCNS patient and a subject who does not have MCNS (e.g., a MN, FGS, IgA nephropathy, or MPGN patient). Any one or combination of markers described above can be used for aiding MCNS diagnosis. Compared to the current MCNS tests available, the present methods provide a quick and simple way to differentiate if a subject has MCNS or MN, FGS, IgA nephropathy, or MPGN, and thus aiding a MCNS diagnosis. The methods comprise: (a) determining a test amount of a marker in a sample from the subject; and (b) determining whether the test amount is a diagnostic amount consistent with a diagnosis of MCNS.

In step (a), a test amount of a marker in a sample from a subject is determined. Any suitable samples can be obtained from a subject. Preferably, a sample is a biological fluid sample taken from a subject being tested. Examples of biological fluid samples include blood, serum, urine, semen, seminal fluid or tissue extracts. Moreover, testing a serum sample does not require an invasive procedure, such as a biopsy.

After a sample is obtained, any suitable method can be used to determine a test amount of the marker in a sample from a subject being tested. For example, gas phase ion spectrometry or an immunoassay can be used.

In one embodiment, gas phase ion spectrometry can be used to determine a test amount of a marker in a sample from a subject. First, one or more markers can be detected with gas phase ion spectrometry using the methods described above. After the marker is detected by a gas phase ion spectrometer, the test amount of marker can be determined. For example, a signal is displayed at the molecular weight of the marker of interest. Based on the strength or magnitude of the displayed signal, the amount of marker in a sample being tested can be determined. It is noted that the test amount of marker in a sample need not be measured in absolute units, but can be in relative units as long as it can be compared qualitatively or quantitatively to a control amount of a marker. For example, as described above, the amount of the marker detected can be displayed in terms of relative intensity based on the background noise. Preferably, the test amount and the control amount of markers are measured under the same conditions.

If desired, the absolute amount of a marker can be determined by calibration. From the peak intensity vs. concentration plot, the absolute amount of a marker in any sample being tested can be determined.

In another embodiment, an immunoassay can be used to determine a test amount of a marker in a sample from a subject. First, a test amount of a marker in a sample can be detected using the immunoassay methods described above. If a marker is present in the sample, it will form all antibody-marker complex with an antibody that specifically binds the marker under suitable incubation conditions described above. The amount of an antibody-marker complex can be determined by comparing to a standard. As noted above, the test amount of marker need not be measured in absolute units, as long as the unit of measurement can be compared to a control amount.

After a test amount of marker is determined using either method, then based on the test amount, it can be determined whether a subject has MCNS. This determination can be made by any suitable methods. For example, the test amount can be compared to a control amount which can be a value or a range of values determined as follows.

In one embodiment, the control amount can be an amount of a marker present in comparable samples from MN, FGS, IgA nephropathy, or MPGN patients. The control amount is measured under the same or substantially similar experimental conditions as in measuring the test amount. For example, if a test sample is obtained from a subject's serum and a marker is detected using a particular probe, then a control amount of the marker is preferably determined from a serum sample of a MN, FGS, IgA nephropathy, or MPGN patient using the same probe. It is preferred that the control amount of marker is determined based upon a significant number of samples from subjects who do not have MCNS (e.g., MN, FGS, IgA nephropathy, or MPGN patients) so that it reflects variations of the marker amounts in that population. If the test amount of marker is significantly increased compared to the control amount of marker which is known to be elevated in samples of MCNS patients (e.g., 5753 Da), then it can be a positive indication that a subject being tested has MCNS. For example, if the test amount is increased by 1.5 fold, preferably by 2 fold, more preferably by 5 fold, or most preferably by 10 fold compared to the control amount, then the test amount is a diagnostic amount which is consistent with a diagnosis of MCNS. The converse would apply for markers that are known to be elevated in the samples of MN, FGS, IgA nephropathy, or MPGN patients than MCNS patients (e.g., 3600 Da).

In another embodiment, a control amount can be an amount of a marker present in comparable samples from a MCNS patient. Again, it is preferred that the control amount of a marker is determined based upon a significant number of samples taken from MCNS patients so that it reflects variations of the marker amounts in that population. If the test amount of the marker is about the same as the control amount of the marker, then it can be a positive indication that a subject being tested has MCNS.

In yet another embodiment, a control amount can be an mount of a marker present in comparable samples from a normal person (i.e., who is known to be free of MCNS and MN, FGS, IgA nephropathy, or MPGN). It is preferred that the control amount of marker is determined based upon a significant number of samples taken from normal persons so that it reflects variations of the marker amounts in that population. If the control amount of a particular marker is significantly lower than the amount of the same marker present in comparable samples of MCNS patients, then this marker can be used to diagnose MCNS and rule out MN, FGS, IgA nephropathy, or MPGN in a single test. In such a case, if the test amount of marker is significantly increased compared to the control amount of marker, then it can be a positive indication that a subject being tested has MCNS. For example, if the test amount is increased by 1.5 fold, preferably by 2 fold, more preferably by 5 fold, most preferably by 10 fold compared to the control amount, then the test amount is a diagnostic amount which is consistent with a diagnosis of MCNS. The converse would apply for markers that are known to be elevated in the samples of MN, FGS, IgA nephropathy, or MPGN patients than MCNS patients.

Data generated by mass spectrometry can then be analyzed by a computer software. The software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and MCNS and determines the closeness of fit between the two signals. The software also can include code indicating which the test sample is closest to, thereby providing a probable diagnosis.

III. Kits

In yet another aspect, the invention provides kits for aiding a diagnosis of MCNS, wherein the kits can be used to detect the markers of the present invention. For example, the kits can be used to detect any one or combination of markers described above, which markers are differentially present in samples of a MCNS patient and a MN, FGS, IgA nephropathy, or MPGN patient. The kits may be used to detect any one or a combination of markers, which markers are differentially present in samples obtained from a patient before and after treatment. The kits of the invention have many applications. For example, the kits can be used to differentiate if a subject has MCNS or MN, FGS, IgA nephropathy, or MPGN, thus aiding a MCNS diagnosis. In another example, the kits can be used to determine if a patient is responding to treatment. In another example, the kits can be used to identify compounds that modulate expression of the markers in in vivo animal models for MCNS.

In one embodiment, a kit comprises: (a) a substrate comprising an adsorbent thereon, wherein the adsorbent is suitable for binding a marker, and (b) a washing solution or instructions for making a washing solution, wherein the combination of the adsorbent and the washing solution allows detection of the marker using gas phase ion spectrometry. Such kits can be prepared from the materials described above, and the previous discussion of these materials (e.g., probe substrates, adsorbents, washing solutions, etc.) is fully applicable to this section and need not be repeated.

In some embodiments, the kit may comprise a first substrate composing an adsorbent thereon (e.g., a particle functionalized with an adsorbent) and a second substrate onto which the first substrate can be positioned to form a probe which is removably insertable into a gas phase ion spectrometer. In other embodiments, the kit may comprise a single substrate which is in the form of a removably insertable probe with adsorbents on the substrate.

Optionally, the kit can further comprise instructions for suitable operational parameters in the form of a label or a separate insert. For example, the kit may have standard instructions informing a consumer how to wash the probe after a sample of serum is contacted on the probe.

In another embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and need not be repeated.

In either embodiment, the kit may optionally further comprise a standard or control information so that the test sample can be compared with the control information standard to determine if the test amount of a marker detected in a sample is a diagnostic amount consistent with a diagnosis of MCNS.

EXAMPLES

The following examples are offered by way of illustration, not by way of limitation.

A. Identification of Markers Using IMAC3-Cu ProteinChip® Array

The Immobilized Metal Affinity Capture array, called "IMAC3" arrays (Ciphergen Biosystems, Inc., Fremont, Calif. USA), can be used to capture molecules that bind divalent cationic metals such as nickel, gallium, copper and zinc. The active spots contain nitrilotriacetic acid groups on the surface that chelate the metal ions. Proteins applied to the chip surface may bind to the chelated metal ion through histidine, tryptophan, cysteine, and phosphorylated amino acids.

Since IMAC3 chips are manufactured in a metal-free form, IMAC3-Cu chips were prepared as follows. Each spot was outlined using a hydrophobic pen and allowed to dry. The chip was then assembled in the bioprocessor. After loading 50 µl of 100 mM copper sulfate to each spot, the chip was shaken for 5 minutes, the excess copper was removed with running deionized water, and the chip was shaken for 5 minutes with an excess of 50 mM sodium acetate, pH 4. The chip was further rinsed under running deionized water. Binding buffer (PBS) was applied to each spot and shaken for 5 min. The surface was wiped dry around the spots and removed excess buffer without touching the active surface. IMAC3-Cu comprising a chelated copper metal ion as an adsorbent was thus prepared.

Serum samples were obtained from patients with MCNS, MN, FGS, IgA nephropathy or MPGN. 0.5 µl of each serum sample was diluted 1/10 with 45 µl of PBS.

The diluted sample solution was added to a spot of adsorbent of IMAC3-Cu. The chip was shaken for 20 min. Each spot was washed with 200 µl PBS three times and the chip was removed from the bioprocessor. After rinsing with water and being dried, 5 µl of saturated sinapinic acid was applied on the spots twice as a matrix. The chip was analyzed with the ProteinChip® System (Ciphergen Biosystems, Inc.).

Figure 1B:
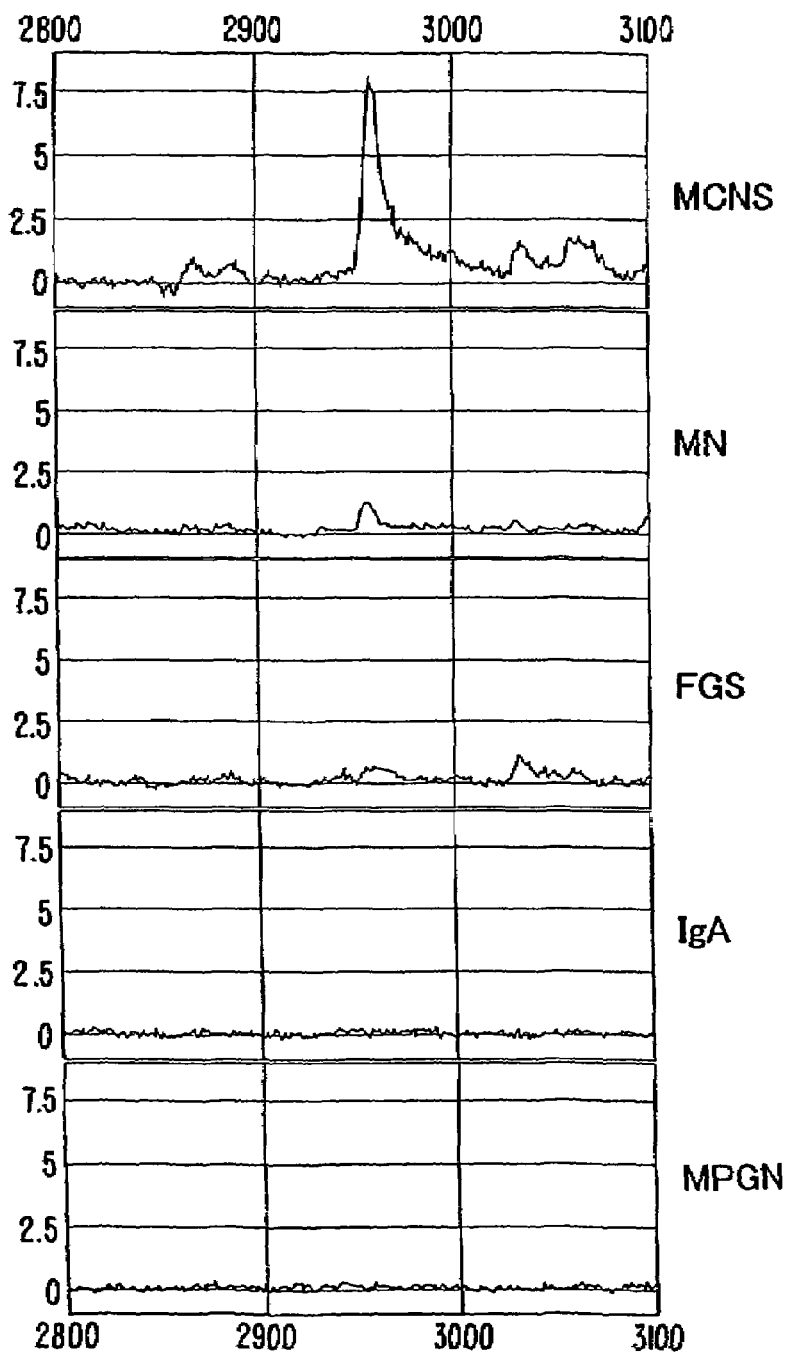
FIG. 1B is an expanded view of a representative example in FIG. 1A.
Figure 2A:
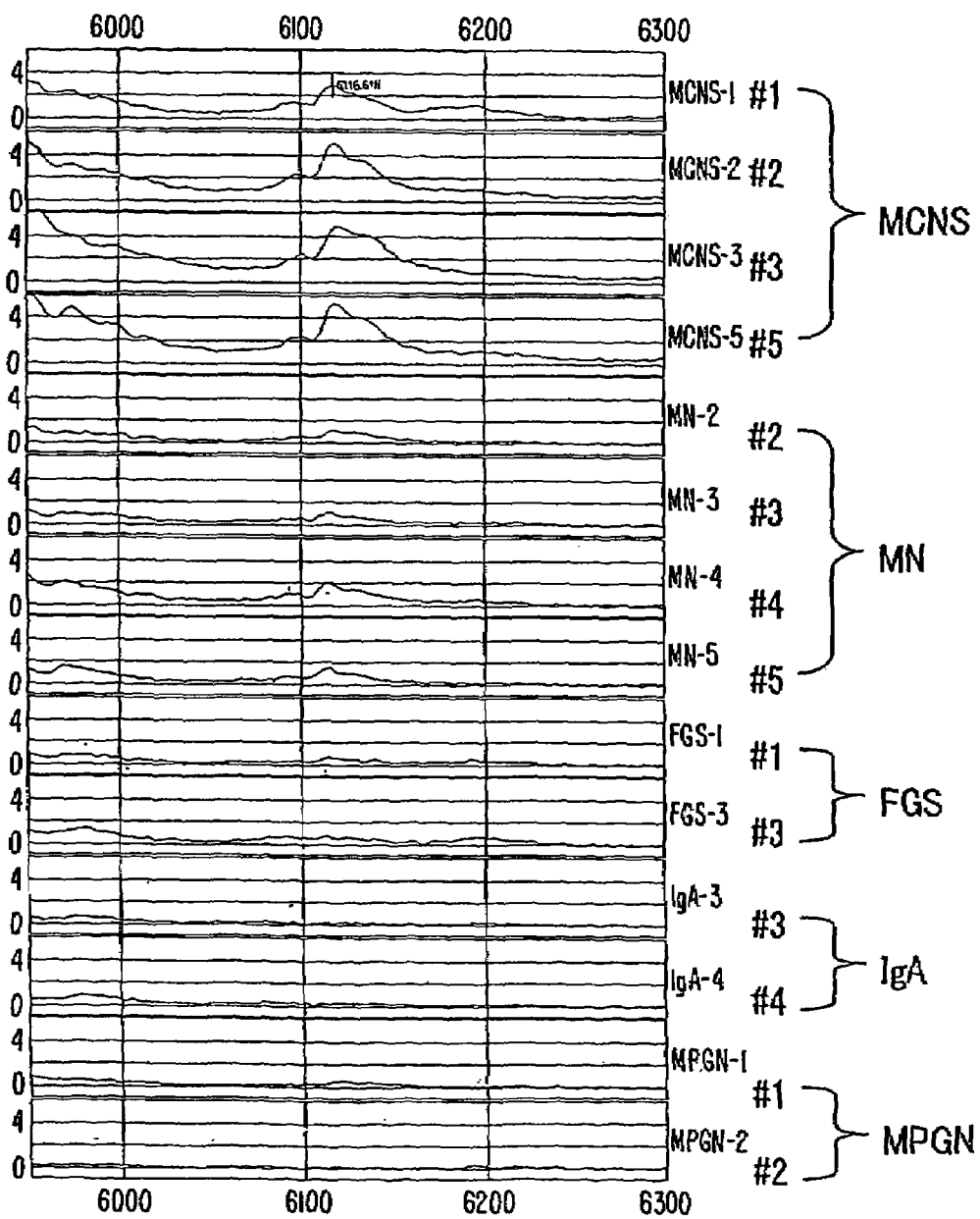
FIG. 2A is a graph comparing four examples of MCNS with four examples of MN, two examples of FGS, two examples of IgA nephropathy and two examples of MPGN.
Figure 2B:
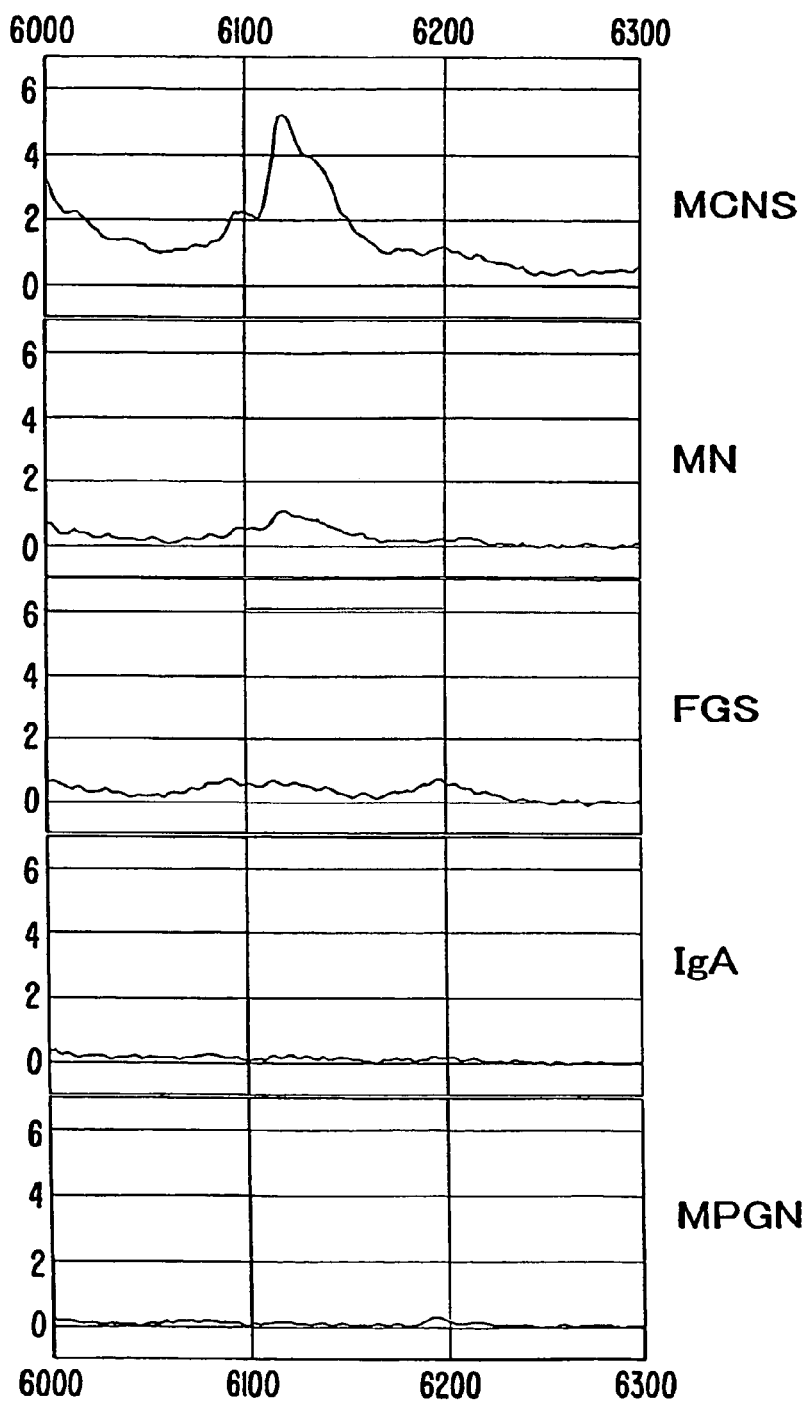
FIG. 2B is an expanded view of a representative example in FIG. 2A.
Figure 3A:
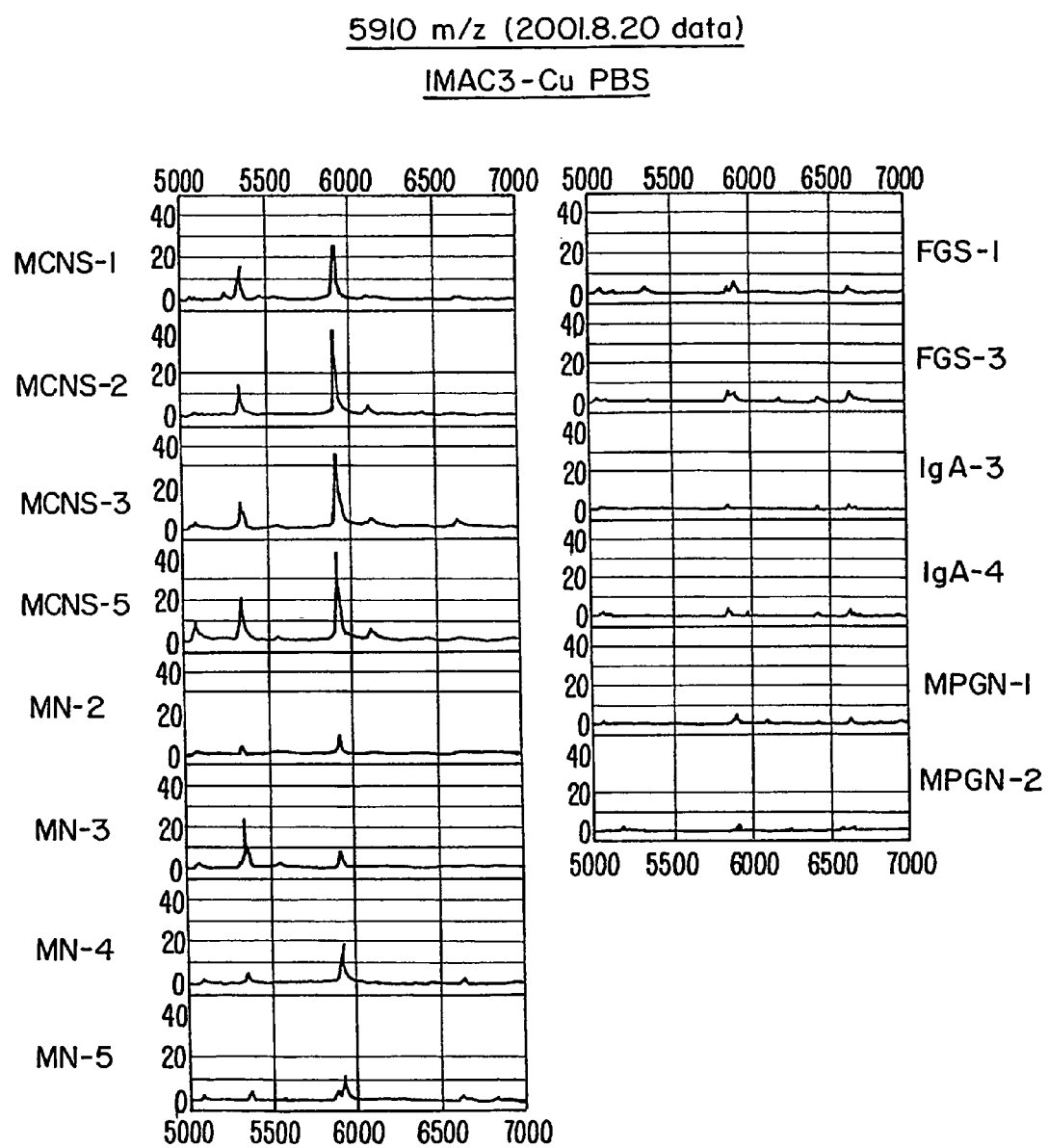
FIG. 3A is a graph comparing four examples of MCNS with four examples of MN, two examples of FGS, two examples of IgA nephropathy and two examples of MPGN.
Figure 3B:
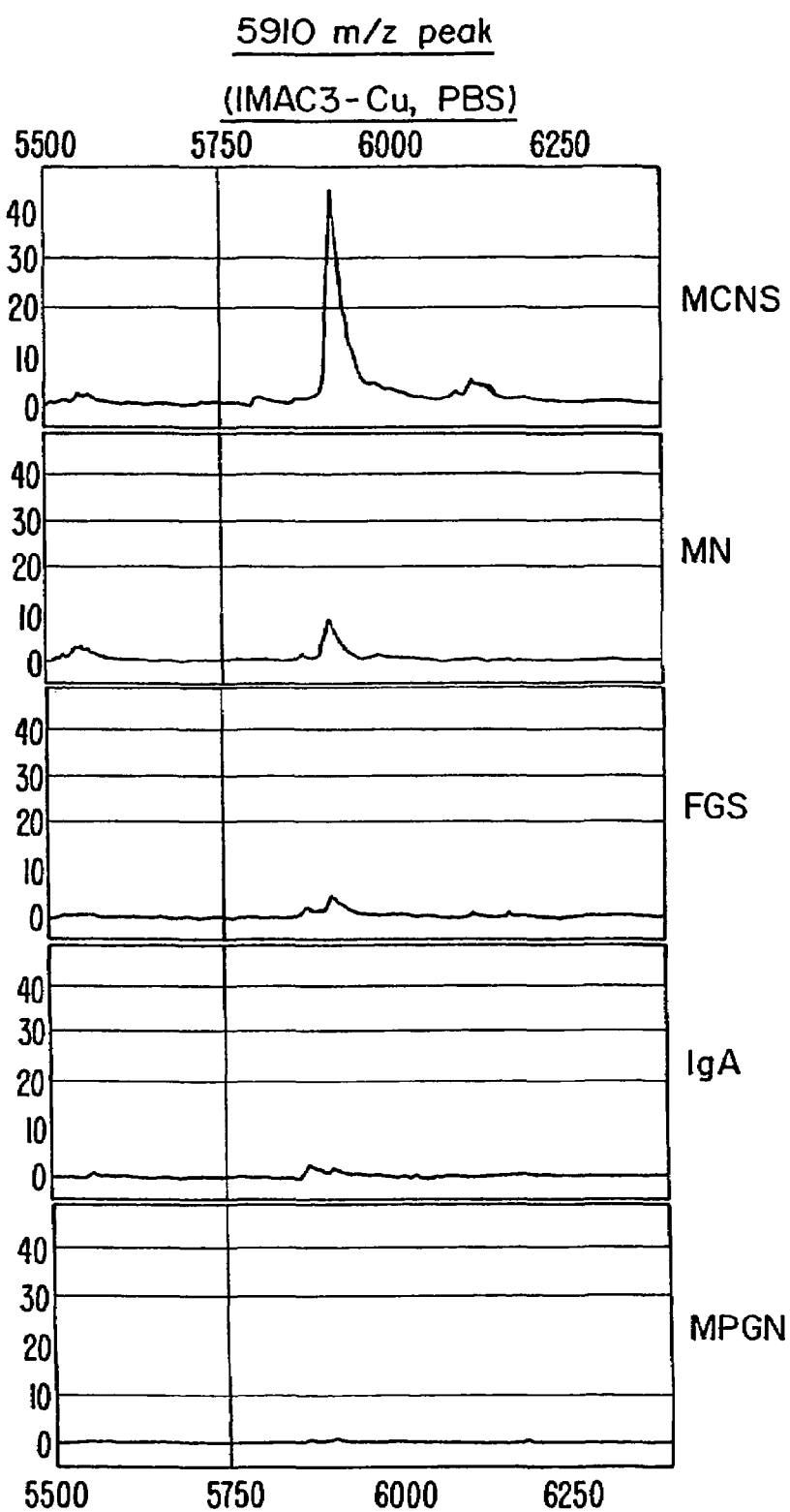
FIG. 3B is an expanded view of a representative example in FIG. 3A.

FIGS. 1, 2, and 3 illustrate the results. As shown in FIGS. 1 and 2, proteins of apparent molecular weight of about 2955 Da (DA-1) and 6117 Da (DA-2) were found to be very abundant in samples from MCNS patients than samples from patients of other diseases.

B. Identification of Markers Using WCX2 ProteinChip® Array

The Weak Cation Exchange array, called "WCX2" arrays can be used to analyze molecules with a positive charge on the surface. The active spots contain weak anionic carboxylate groups that interact with the positive charges on the surface on the analyte, e.g., lysine, arginine or histidine. The chip was assembled in the bioprocessor, and was incubated for 5 minutes with binding buffer (200 µl of 50 mM sodium acetate for pH4 and 50 mM sodium phosphate for pH6). The incubation was repeated twice.

Serum samples were prepared using substantially the same solutions and procedures described above. The diluted sample solution was added to a spot of adsorbent of WCX2. After the chip was shaken for 20 minutes, each spot was washed with binding buffer three times, and the chip was removed from the bioprocessor. The spots were further rinsed with water, dried, and applied sinapinic acid as a matrix. The chip was analyzed with the ProteinChip® System (Ciphergen Biosystems, Inc.)

Figure 4A:
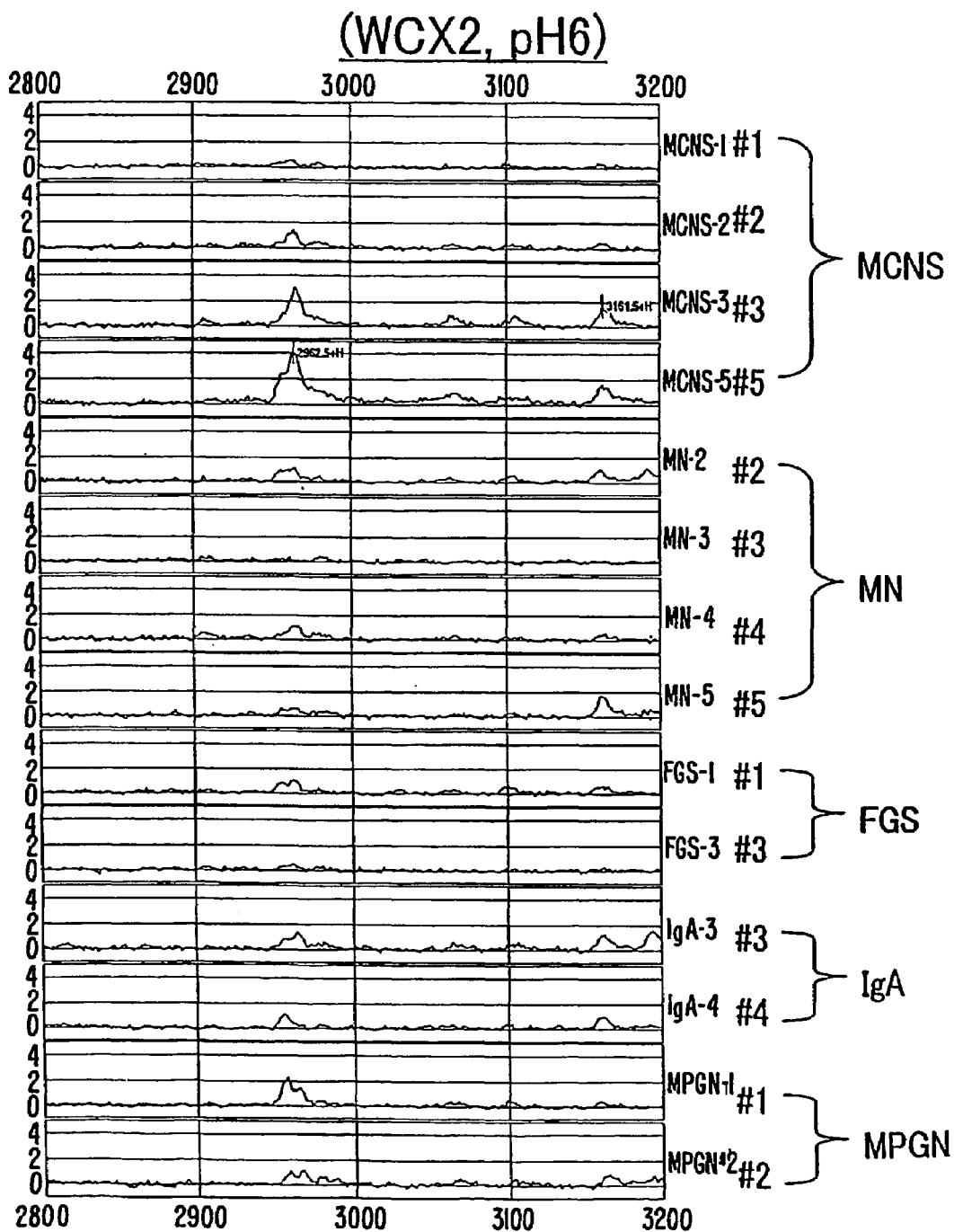
FIG. 4A is a graph comparing four examples of MCNS with four examples of MN, two examples of FGS, two examples of IgA nephropathy and two examples of MPGN.
Figure 4B:
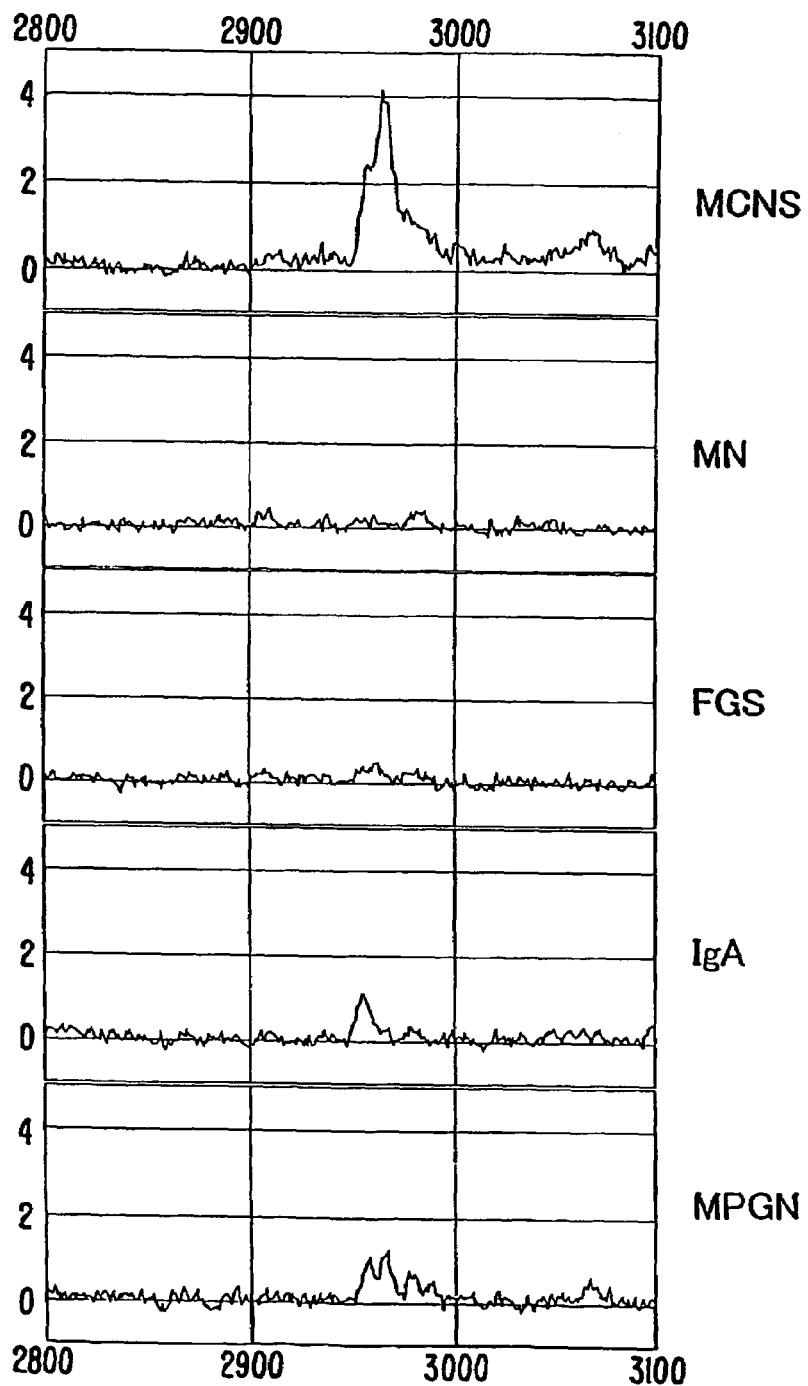
FIG. 4B is an expanded view of a representative example relating to the peak at 2962.5 Da (DB-1) in FIG. 4A.
Figure 4C:
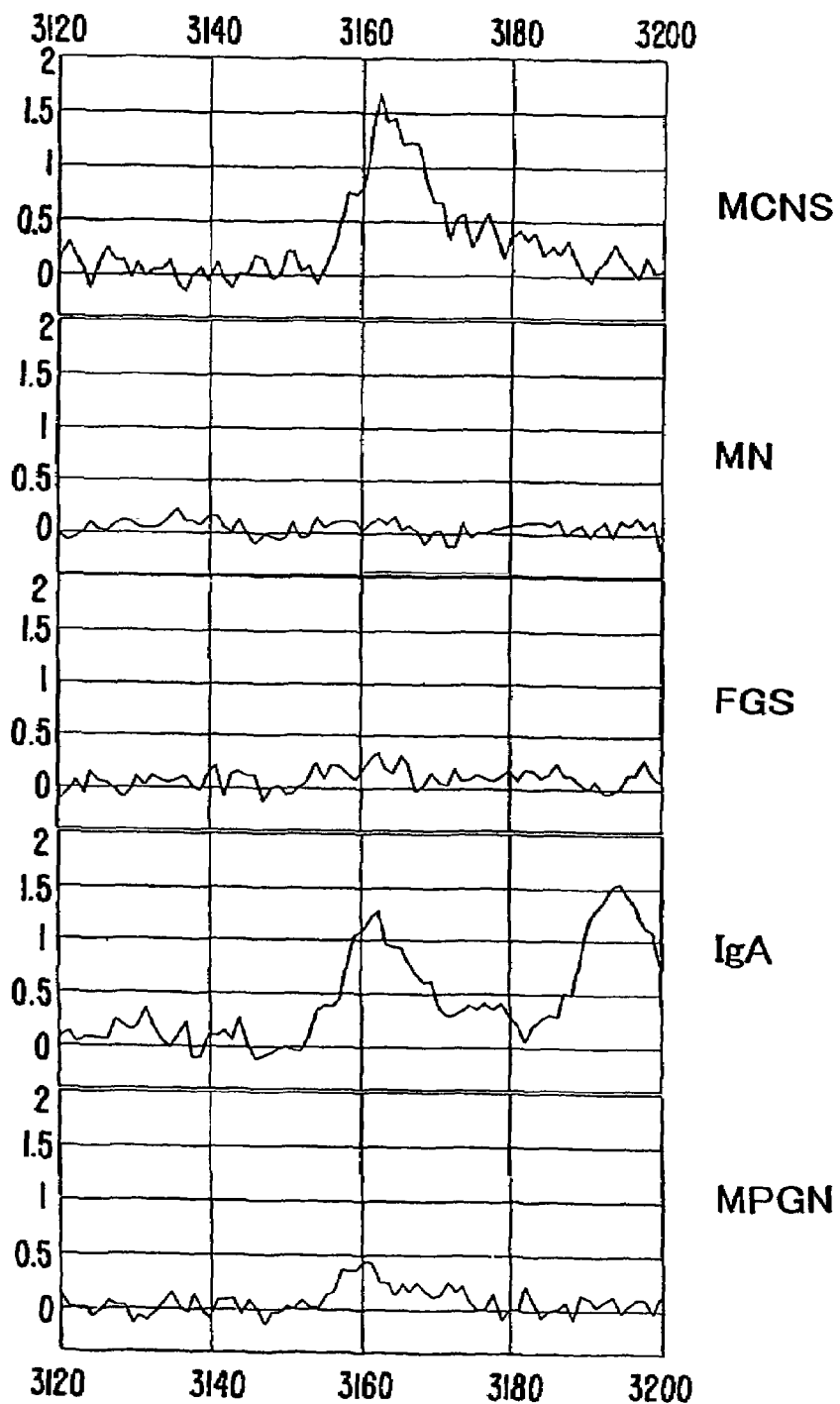
FIG. 4C is an expanded view of a representative example relating to the peak at 3161.5 Da (DB-3) in FIG. 4A.
Figure 5A:
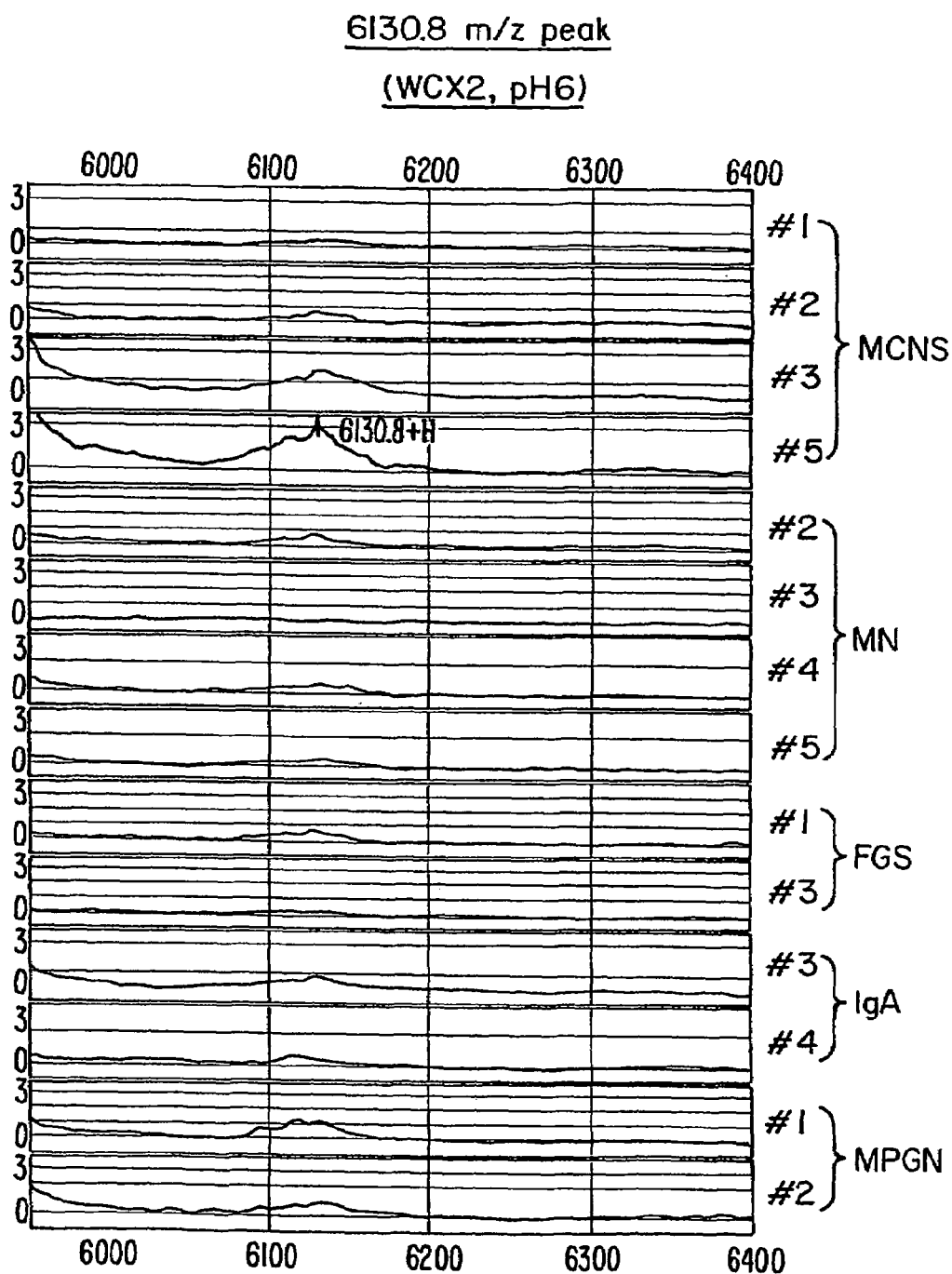
FIG. 5A is a graph comparing four examples of MCNS with four examples of MN, two examples of FGS, two examples of IgA nephropathy and two examples of MPGN.
Figure 5B:
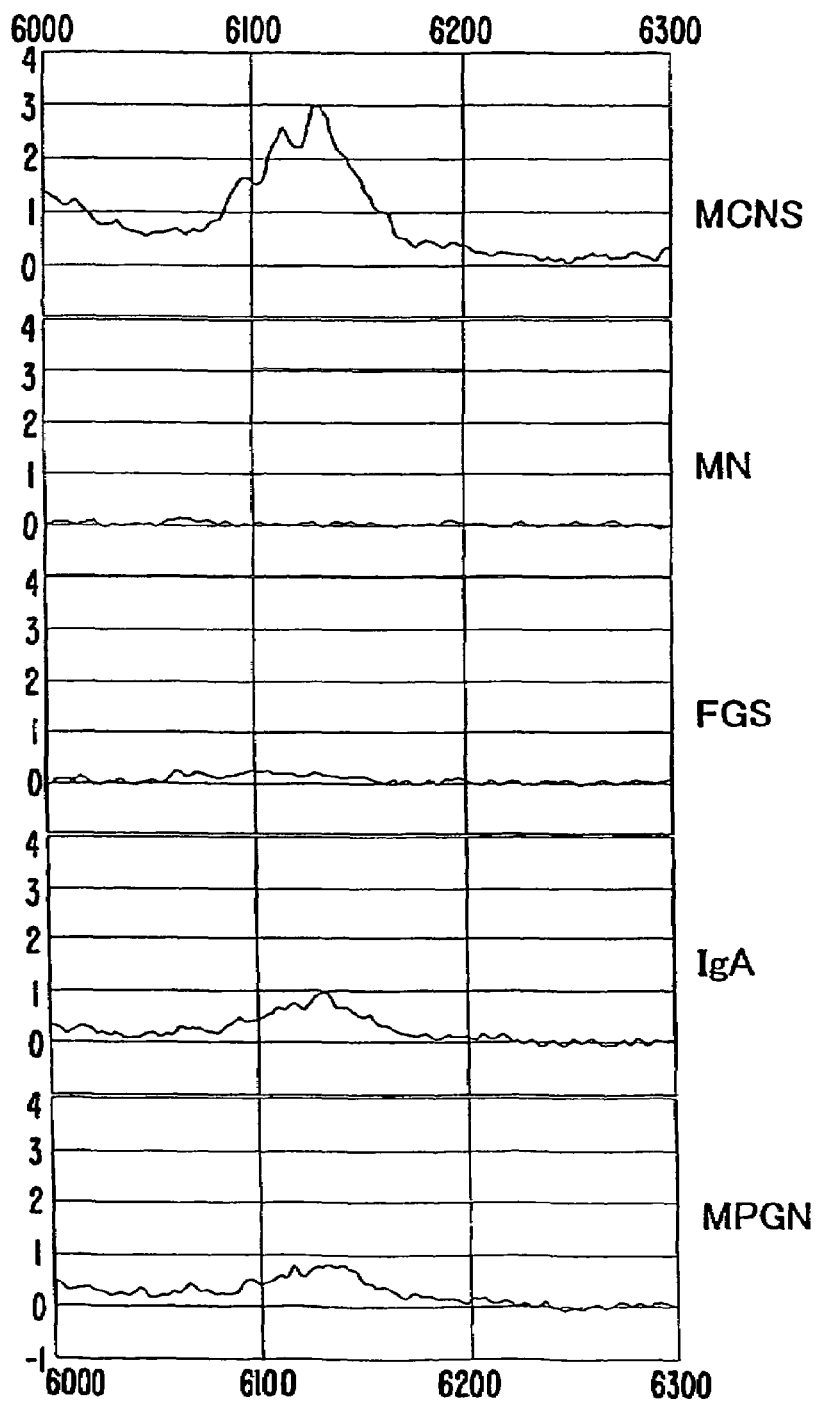
FIG. 5B is an expanded view of a representative example in FIG. 5A.

FIGS. 4 and 5 illustrate the results. As shown in FIGS. 4 and 5, proteins of apparent molecular weight of about 2963 Da (DB-1), 3162 Da (DB-2) and 6131 Da (DB-3) were found to be very abundant in samples from MCNS patients than samples from patients of other diseases.

C. Identification of Markers for Evaluating the Therapeutic Value of Agents for Treating Kidney Disease Using IMAC3-Cu, WCX2 and SAX2 ProteinChip® Array IMAC3-Cu chip and WCX2 chip were prepared and used in substantially the same methods described above.

The strong Anion Exchange array, called the "SAX2" chip, can be used to analyze molecules with a negative charge on the surface. The active spots contain cationic, quaternary ammonium groups that interact with the negative charges on the surface of target proteins, e.g., aspartic acid or glutamic acid. The chip was assembled in the bioprocessor and 200 µl binding buffer (50 mM Tris-HCl for pH8 and 50 mM Sodium phosphate for pH6) was added to each well. The chip was then incubated for 5 minutes at room temperature with vigorous shaking. The buffer was removed from the wells, the sample solution was added immediately, and the chip was incubated with vigorous shaking for 20 minutes. Then, the samples were removed from the wells and the wells were washed three times with binding buffer. The chip was removed from the bioprocessor, rinsed with water and air-dried. After applying sinapinic acid as a matrix, the chip was analyzed with the ProteinChip® System (Ciphergen Biosystems, Inc.)

Serum, urine and PBNC samples were obtained from a patient with MCNS before and after the treatment. Serum was diluted to 1/10, urine to 1/5, and PBNC to 1.2 mg/ml.

Figure 6:
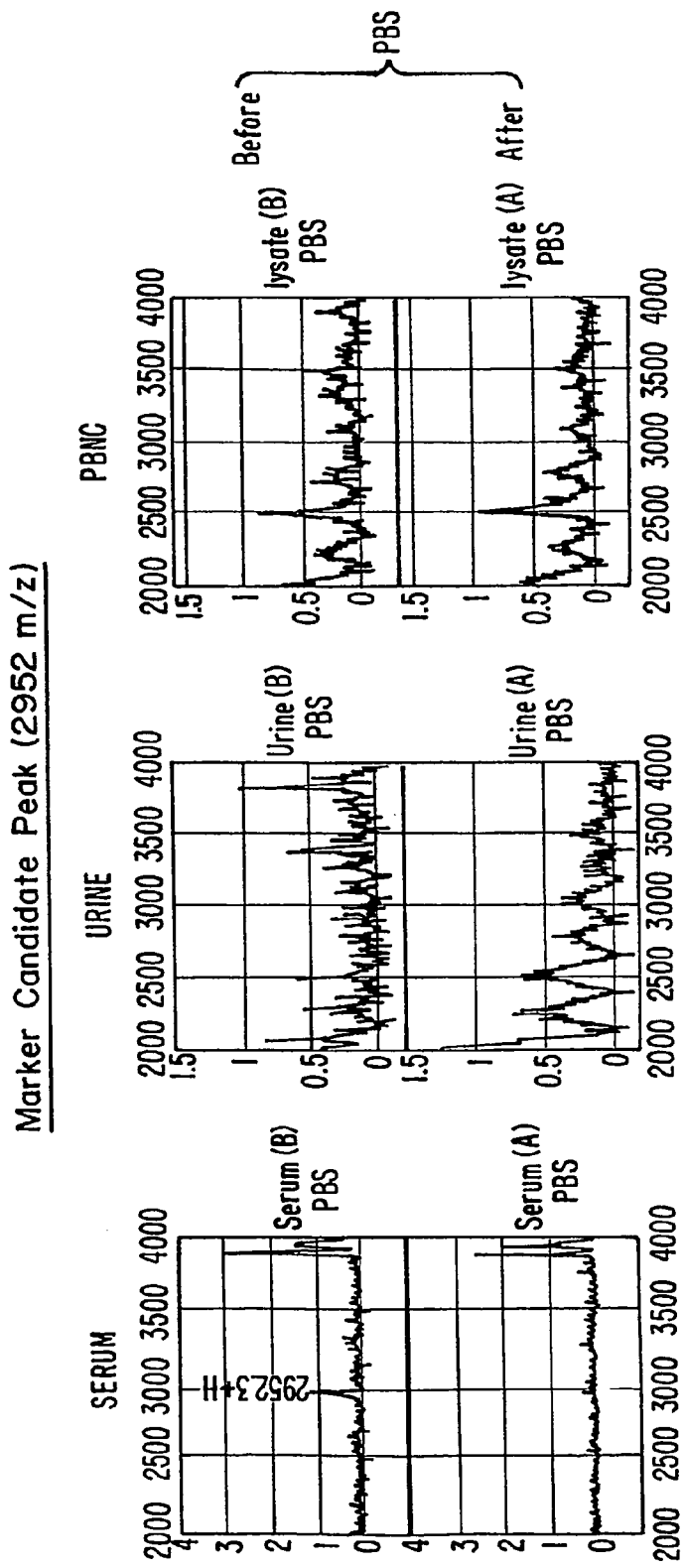
FIG. 6 is a graph comparing values before and after MCNS treatment. Samples of serum, urine and peripheral blood lymphocyte (PBNC) were used.
Figure 7:
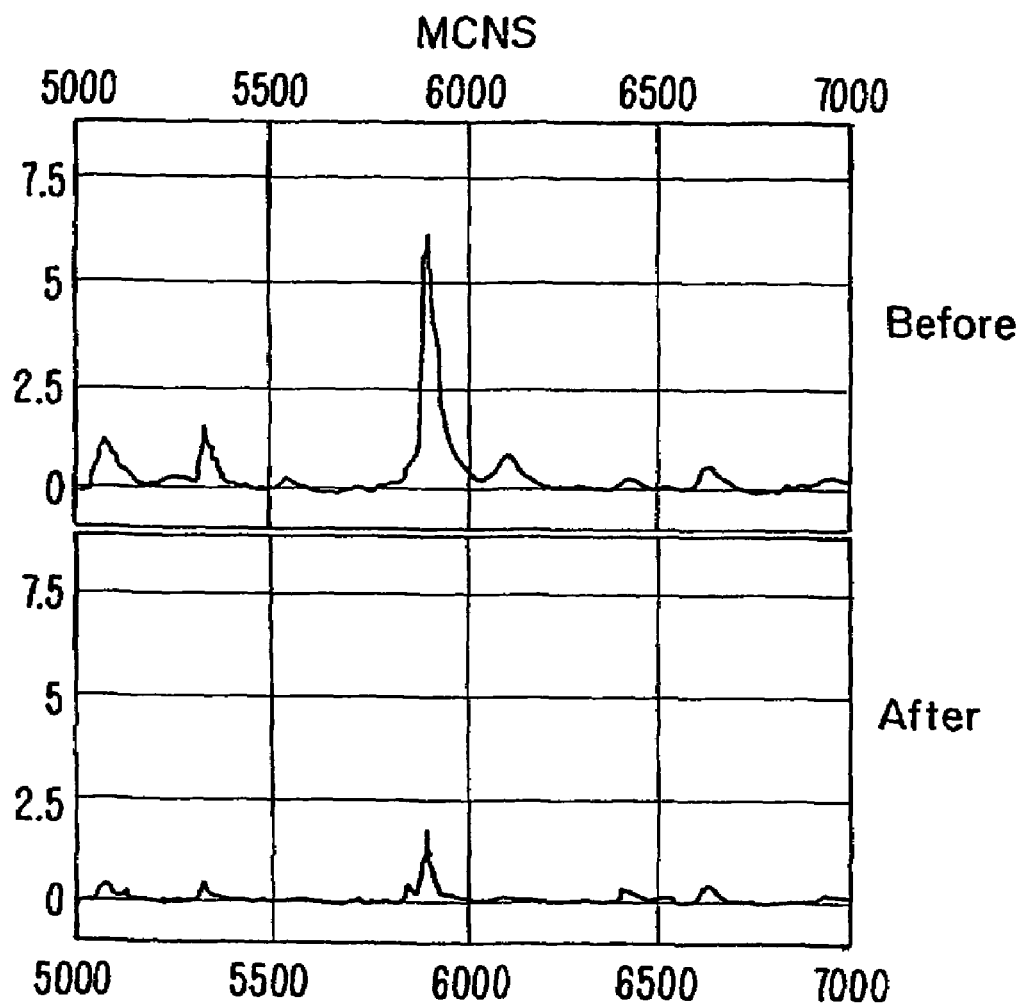
FIG. 7 is a graph comparing values before and after MCNS treatment.

FIGS. 6 and 7 shows the results using IMAC3-Cu chips. In serum sample solution, a protein of about 2952 Da (TA-1) and 5910 Da (TA-2) disappeared after the treatment (FIGS. 6 and 7).

Figure 8:
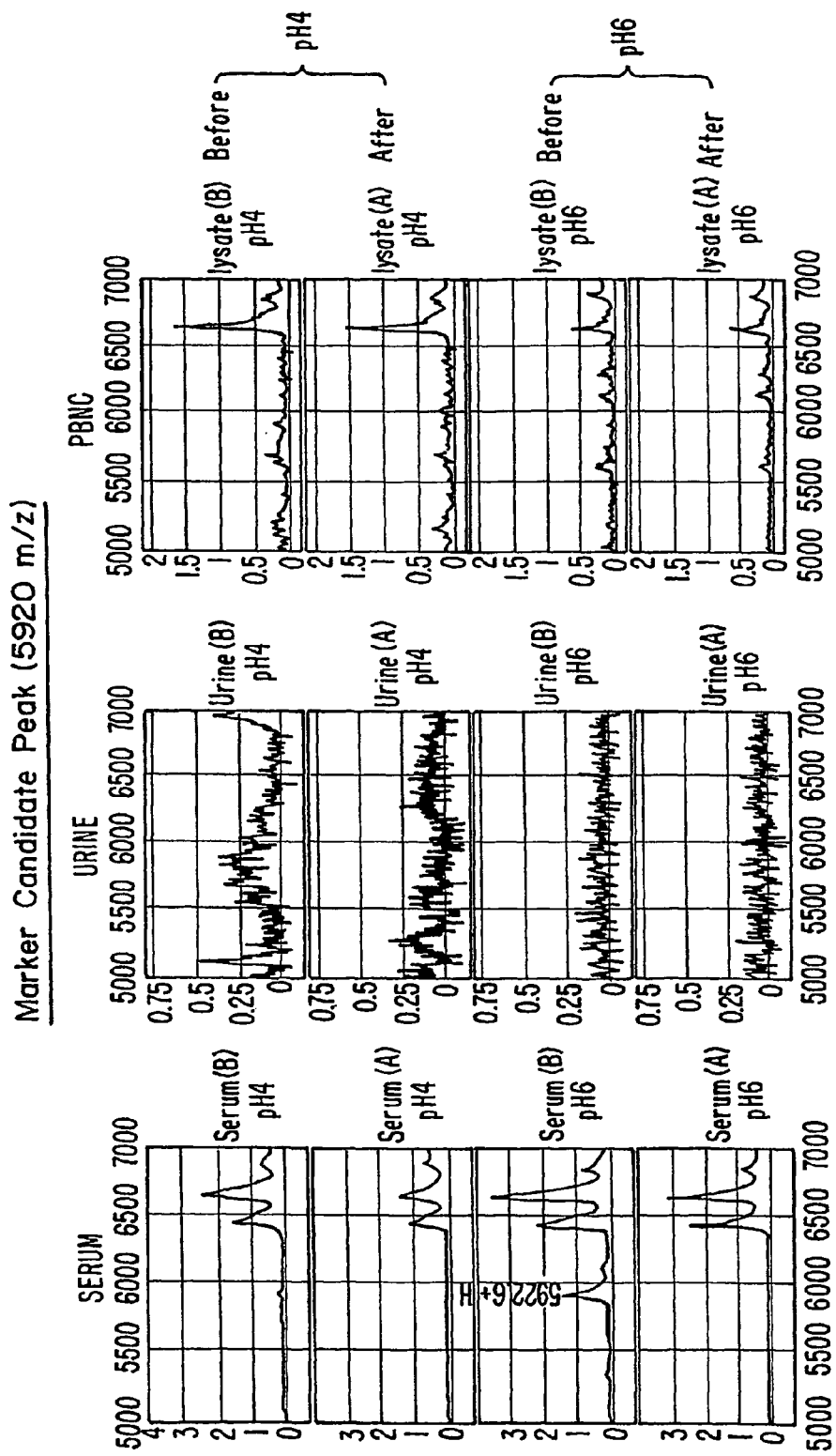
FIG. 8 is a graph comparing values before and after MCNS treatment. Samples of serum, urine and peripheral blood lymphocyte (PBNC) were used.
Figure 9:
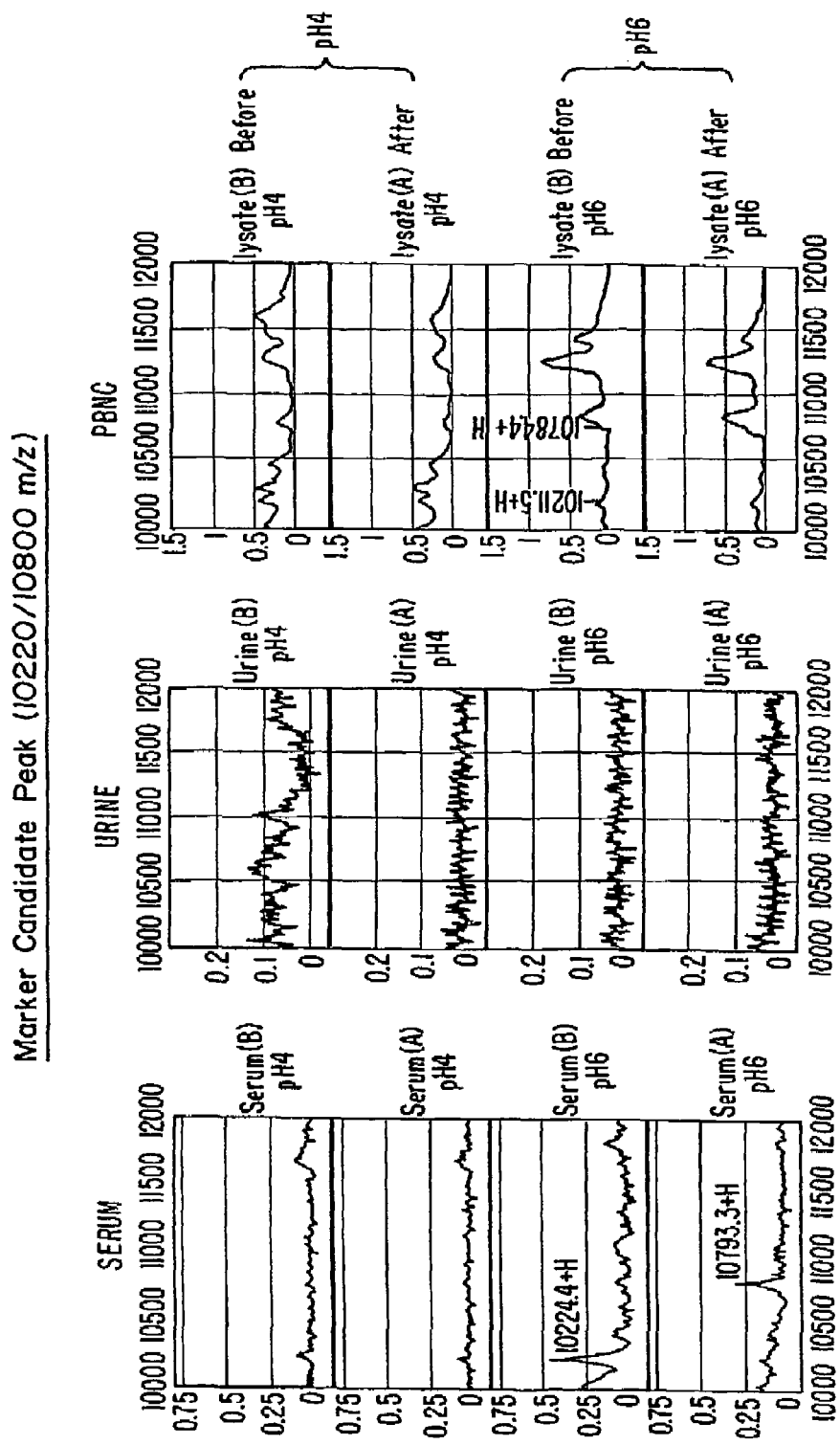
FIG. 9 is a graph comparing values before and after MCNS treatment. Samples of serum, urine and peripheral blood lymphocyte (PBNC) were used.

FIGS. 8 and 9 illustrate the results using WCX2 chips. When using pH6 buffer, proteins of apparent molecular weight of about 5923 Da (TB-1) and 10224 Da (TB-2) in serum sample vanished after the treatment (FIGS. 8 and 9) and a protein of about 10793 Da (TB-3) appeared to the contrary.

Figure 10:
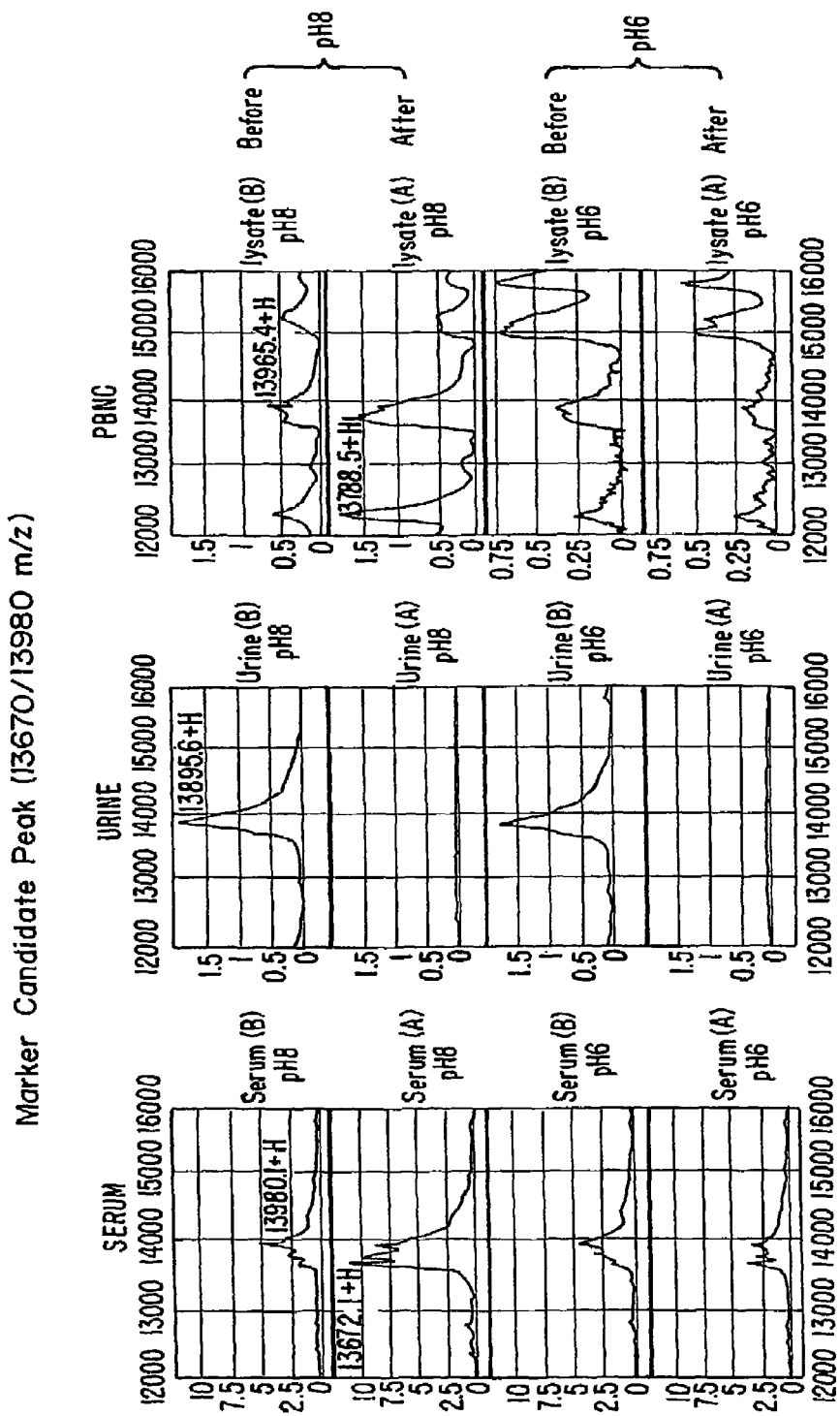
FIG. 10 is a graph comparing values before and after MCNS treatment. Samples of serum, urine and peripheral blood lymphocyte (PBNC) were used.

FIG. 10 illustrates the results using SAX2 chips. As shown in FIG. 10, the ratio of a protein of apparent molecular weight of about 13980 Da (TC-2) to a protein of about 13672 Da (TC-1) in serum sample solution was reversed after the treatment. As shown in FIG. 10, a protein of apparent molecular weight of about 13896 Da (TC-3) in urine sample vanished after the treatment. When using pH8 buffer, the ratio of a protein of about 13965 Da (TC-5) to a protein of 13789 Da (TC-4) in PBNC sample was reversed after the treatment (FIG. 10).

D. Identification of Markers by Protein Ladder Sequencing

One marker, the 5910 Da marker (DA-3 and TA-2) was identified by protein ladder sequencing. Serum proteins containing the marker were separated on polyacrylamide gels, electroblotted onto Immobilon-PSQ PVDF membrane (SIGMA), the band corresponding to the 5910 Da marker was isolated and the N-Terminal amino acid sequence was identified. A comparison of the N-Terminal sequence with the publicly available databases indicated that the 5910 Da marker was the α-2-HS glycoprotein β chain (mature form) (see Haglund et al., Biochemical Journal 357:437-445 (2001)). A minor component also was found in the band and identified to be human apolipoprotein AII. Polyclonal and monoclonal antibodies directed against the 5910 Da marker may be made as described in section I. B. by immunizing rabbits or mice with the whole 5910 Da marker or with peptides derived from the marker. These new antibodies, or existing polyclonal or monoclonal antibodies may be used in the immunoassays described in section I. B. to quantitatively and qualitatively detect and analyze the marker in diagnostic and treatment samples. Polyclonal and monoclonal antibodies directed against the 5910 Da marker may be bound to a substrate and used as a specific adsorbent for gas phase ion spectrometry detection described in section I. A. to quantitatively and qualitatively detect and analyze the marker in diagnostic and treatment samples.

The present invention provides novel materials and methods for aiding MCNS diagnosis using markers that are differentially present in samples of a MCNS patient and a subject who does not have MCNS. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A method of diagnosing minimal change nephrotic syndrome in a patient having kidney disease, the method comprising:
   (a) obtaining a sample from an idiopathic nephrotic syndrome patient;
   (b) detecting alpha-2-HS glycoprotein beta chain in the sample from the patient; and
   (c) correlating elevation of the alpha-2-HS glycoprotein in the sample with a control amount to diagnose minimal change nephrotic syndrome.

2. The method of claim 1, wherein detection is performed by immunoassay.

3. The method of claim 1, wherein detection is performed by SELDI MS mass spectrometry.

4. The method of claim 1 where the sample is blood serum.

* * * * *